(12) United States Patent
Smisson, III et al.

(10) Patent No.: US 8,109,906 B2
(45) Date of Patent: Feb. 7, 2012

(54) CONTROL OF A PUMP DEVICE

(75) Inventors: Hugh F. Smisson, III, Macon, GA (US); Richard G. Cartledge, Fort Lauderdale, FL (US); David C. Field, Snellville, GA (US); Frederick J. York, Longwood, FL (US)

(73) Assignee: Smisson-Cartledge Biomedical LLC, Macon, GA (US)

( * ) Notice: Subject to any disclaimer, the term of this patent is extended or adjusted under 35 U.S.C. 154(b) by 689 days.

(21) Appl. No.: 11/835,132

(22) Filed: Aug. 7, 2007

(65) Prior Publication Data

US 2008/0146996 A1      Jun. 19, 2008

Related U.S. Application Data

(63) Continuation-in-part of application No. 11/082,260, filed on Mar. 17, 2005, now Pat. No. 7,563,248.

(51) Int. Cl.
*A61M 1/00* (2006.01)
*A61M 37/00* (2006.01)
*F04B 43/08* (2006.01)
*F04B 43/12* (2006.01)
*F04B 43/06* (2006.01)

(52) U.S. Cl. ............... 604/122; 604/131; 417/477.2
(58) Field of Classification Search ............ 604/131, 604/65–67, 122; 417/477.2
See application file for complete search history.

(56) References Cited

U.S. PATENT DOCUMENTS

| | | | |
|---|---|---|---|
| 3,590,215 A | 6/1971 | Anderson et al. | |
| 4,370,983 A | 2/1983 | Lichtenstein | |
| 4,475,901 A | 10/1984 | Kraegen et al. | |
| 4,537,561 A | 8/1985 | Xanthopoulos | |
| 4,747,826 A | 5/1988 | Sassano | |
| 4,847,470 A | 7/1989 | Bakke | |
| 4,874,359 A | 10/1989 | White et al. | |
| 4,981,467 A | 1/1991 | Bobo, Jr. et al. | |
| 5,061,241 A | 10/1991 | Stephens, Jr. et al. | |
| 5,104,374 A | 4/1992 | Bishko et al. | |
| 5,125,069 A | 6/1992 | O'Boyle | |

(Continued)

FOREIGN PATENT DOCUMENTS

WO     WO97/21456 A1    6/1997

OTHER PUBLICATIONS

U.S. Appl. No. 11/835,095, filed Aug. 7, 2007, Smisson III et al.

(Continued)

*Primary Examiner* — Nicholas D Lucchesi
*Assistant Examiner* — Rebecca E Eisenberg
(74) *Attorney, Agent, or Firm* — Sutherland Asbill & Brennan LLP

(57) ABSTRACT

A pump system simply and selectably controls the temperature, flow rate, flow volume, and flow pressure of a fluid being infused into a patient's body. The pump system a includes a central controller and user inputs that allow for simple selection and efficient operation of the pump system, which includes manually or automatically priming the pump system to remove air, selectably controlling and rapidly adjusting the flow rate over a wide range, selectably and safely controlling the pump system temperature controls, and selectably controlling the flow pressure during delivery. The pump system includes a pump housing with a central controller and a cartridge with infusion tubing removably coupled to the pump housing.

18 Claims, 18 Drawing Sheets

U.S. PATENT DOCUMENTS

| | | |
|---|---|---|
| 5,181,910 A | 1/1993 | Scanlon |
| 5,245,693 A | 9/1993 | Ford et al. |
| 5,273,517 A | 12/1993 | Barone et al. |
| 5,311,908 A | 5/1994 | Barone et al. |
| 5,366,346 A | 11/1994 | Danby |
| 5,381,510 A | 1/1995 | Ford et al. |
| 5,385,540 A | 1/1995 | Abbott et al. |
| 5,429,602 A | 7/1995 | Hauser |
| 5,464,391 A | 11/1995 | DeVale |
| 5,482,446 A | 1/1996 | Williamson et al. |
| 5,514,095 A | 5/1996 | Brightbill et al. |
| 5,573,502 A | 11/1996 | LeCocq et al. |
| 5,586,085 A | 12/1996 | Lichte |
| 5,590,654 A | 1/1997 | Prince |
| 5,591,251 A | 1/1997 | Brugger |
| 5,645,531 A | 7/1997 | Thompson et al. |
| 5,656,027 A | 8/1997 | Ellingboe |
| 5,746,719 A | 5/1998 | Farra et al. |
| 5,782,805 A | 7/1998 | Meinzer et al. |
| 5,800,387 A | 9/1998 | Duffy et al. |
| 5,857,843 A | 1/1999 | Leason et al. |
| 5,863,421 A * | 1/1999 | Peter, Jr. et al. .............. 210/134 |
| 5,876,370 A | 3/1999 | Blomquist |
| 6,074,363 A | 6/2000 | Beran et al. |
| 6,175,688 B1 | 1/2001 | Cassidy et al. |
| 6,236,809 B1 | 5/2001 | Cassidy et al. |
| 6,259,074 B1 | 7/2001 | Brunner et al. |
| 6,270,478 B1 | 8/2001 | Mernoe |
| 6,464,666 B1 | 10/2002 | Augustine et al. |
| 6,475,178 B1 | 11/2002 | Krajewski et al. |
| 6,480,257 B2 | 11/2002 | Cassidy et al. |
| 6,622,542 B2 | 9/2003 | Derek et al. |
| 6,719,779 B2 | 4/2004 | Daoug |
| 6,775,473 B2 | 8/2004 | Augustine et al. |
| 7,004,924 B1 | 2/2006 | Brugger et al. |
| 2005/0022274 A1 | 1/2005 | Campbell et al. |
| 2005/0209563 A1 | 9/2005 | Hopping et al. |
| 2006/0211988 A1 | 9/2006 | Smisson, III et al. |
| 2008/0015507 A1 | 1/2008 | Cartledge et al. |

OTHER PUBLICATIONS

U.S. Appl. No. 11/835,118, filed Aug. 7, 2007, Smisson III et al.
U.S. Appl. No. 11/835,125, filed Aug. 7, 2007, Smisson III et al.

* cited by examiner

CONTROL OF A PUMP DEVICE

RELATED APPLICATION

This application is a continuation-in-part of U.S. patent application Ser. No. 11/082,260 filed Mar. 17, 2005, which is incorporated by reference in its entirety herein.

STATEMENT REGARDING FEDERALLY SPONSORED RESEARCH OR DEVELOPMENT

This invention was made possible at least in part with the assistance of US Grant No. DAMD 17-02-01-0700 awarded by the United States Army, and the government may have certain rights therein.

FIELD OF THE INVENTION

The present invention is directed to an infusion device having a disposable cartridge for warming and/or cooling fluid that connects with a pump housing and allows for simple, accurate control of infusion flow rates and/or infusion pressures.

BACKGROUND

Fluid required in treating a patient must often be stored in comparatively cool to cold temperatures with respect to the patient's body temperature. This often refrigerated storage is necessary to preserve the fluids in a state so the function and integrity of the fluid is maintained. Fluids such as blood and other bodily fluids are typically stored at hypothermic temperatures ranging from 2° to 20° Celsius. Therefore, when introducing fluids into the patient's body it is often necessary to heat the fluid to an appropriate temperature not only to prevent any rapid decrease in the patient's body temperature, but also to ensure that the fluid being introduced can function as needed. It is known that the injection of cold fluids into a patient's body can create a major source of conductive heat loss within the patient, often placing the patient at further risk by cooling, too quickly or, to a temperature where physiological damage can occur.

In heating or warming the fluid, however, care must be taken to ensure that the heating itself does not create a further complication. For instance, if blood reaches a certain temperature then hemolysis, the destruction or severe degradation, of the blood cells can occur. Likewise, if the fluid is heated too high and then introduced into the patient's body, physiological damage resulting from exposure to excessive temperatures such as burns or other such scarring can occur. Heating the fluid in bulk form usually requires the application of too intense a heat source in order to heat the entire fluid with any level of time efficiency. Likewise, heating the fluid over a prolonged period of time can lead to increased exposure of the material to the environment creating risks of contamination.

Getting the fluid into the patient requires adjustable flow so that the proper amount of fluid depending upon the need is provided to the patient. Combining the fluid delivery means with the proper and efficient heating of the fluid is crucial to the proper delivery of fluid to the patient. The prior art contains systems for warming fluids as they are infused into a patient. The manner in which the fluids are heated within these systems varies and can be accomplished via convection or conduction. An example of a system which poses clinical problems heats the fluid being delivered to the patient via exposure to a heated fluid, such as water. Such systems are usually cumbersome, require frequent cleaning, and can pollute the clinical environment through the introduction of an additional substance—the heating liquid. Such a system often places a conduit through a liquid such as water, which is then heated, and the fluid to be delivered to the patient is drawn through the conduit thereby increasing the temperature of the fluid to be delivered. Such a system can be deleterious to a sterile environment and may not be properly transported. Furthermore, these systems also have large mass, which require significant power to heat that mass yielding a significant time to achieve that temperature, or achieve a stasis when a cold mass (like a bag of chilled fluid) is introduced. An additional problem to be avoided is the danger to the patient caused by current leakage in the system circuitry and specifically the circuitry used to achieve the warming characteristics that may be in close contact to the blood being infused to the patient. Capacitive coupling, the transfer of energy from one element to another by means of mutual capacitance, could possibly cause enough current leakage to the heating system, and, potentially, to the patient and cause electric shock. It is, therefore, important to reduce the amount of capacitive coupling between the heating system and the heating exchanger, thus reducing the potential for current leakage and reducing the risk of causing electric shock to the patient, while at the same time creating efficient heating of the blood.

Moreover, during some fluid infusion procedures it is beneficial to adjust the temperature of the patient's body either warmer or cooler. As such, it is extremely beneficial to have an adjustable in-line fluid warming or cooling system so that the proper temperature can be regulated. In instances of massive or emergent fluid loss, it is often necessary to infuse (and sometimes recover and re-infuse) extremely large amounts of fluid into the patient's body. In such instances traditional fluid heating systems often place the fluid at risk by exposure to temperatures which could damage the fluid because the fluid must be heated so rapidly. Furthermore, whereas existing patient cooling methods include practices such as externally applying cooling blankets, it will be beneficial to provide a system that more efficiently and rapidly cools a patient's core body temperature. Such problems remain largely unsolved by the art; and the need for better incline fluid infusers is abundant.

Similarly, studies have shown that symptoms and harmful effects of certain conditions may be reduced by inducing hypothermia. For example, it has been demonstrated that circulating cooled blood before or during ischemia reduces the infarct size or slows the effects caused by infarction. Similarly, other studies show that cooling patients after suffering an acute stroke reduces metabolism and inflammation, both factors affecting ischemia induced by stroke. Thus, there also exists a need for a means to accurately cool fluid, like blood, and control flow rates of the cooled fluid.

When introducing fluid into a patient's body (e.g., the circulatory system) it is crucial that air not be introduced into the patient's body as well. Introduction of air or air bubbles into a patient's body (e.g., the circulatory system) can cause extremely deleterious effects. Air embolisms can occur if air accumulates in a patient's blood stream resulting in cardiac arrhythmias, stroke, or pulmonary infarct. Any of these potential infirmities can be life threatening and need to be minimized in situations where high volumes of fluid are being infused. It is therefore extremely important that during infusion of fluid that both the monitoring of air in the infusion system occurs to prevent introduction into the patient's body.

Devices in the prior art seeking to warm fluid for infusion into the body often suffer from very specific problems. For example, the heater system described in U.S. Pat. No. 3,590, 215 issued to Anderson et al. uses regions of differing heat which the fluid encounters as it progresses through the system. Specifically, the heating element or elements described in Anderson et al. diminishes the heat in the material warming the fluid from a hottest temperature where the fluid enters the heat exchanger to a coolest temperature where the fluid exits the heat exchanger. Such a configuration not only makes it difficult to regulate the temperature of the fluid as the flow rate changes, but it also runs the risk of having to expose the fluid to temperatures above which the fluid should be exposed to, running the risk of damaging the fluid.

Likewise, the serpentine fluid flow path described in Anderson et al. creates the typical laminar type flow seen in most heat exchanger systems. For example, U.S. Pat. No. 5,245,693 to Ford et al. describes a serpentine flow pattern which is long compared to its width and wider compared to its depth. This type of flow is consistent with a non-turbulent laminar type flow path. A non-turbulent flow path requires additional heat energy to be introduced into the fluid system or longer exposure to the heating in order to increase the temperature of the fluid system uniformly to a desired temperature.

In addition to heating the fluid efficiently, a variety of clinical circumstances, including massive trauma, major surgical procedures, massive burns, and certain disease states such as pancreatitis and diabetic ketoacidosis can produce profound circulatory volume depletion, either from actual blood loss or from internal fluid imbalance. In these clinical settings, it is often necessary to infuse blood or other fluids rapidly into a patient to avert serious consequences.

Intravenous infusion rates may be defined as either routine, generally up to about 999 cubic centimeters per hour, or rapid, generally between about 999 cubic centimeters per hour and about 90,000 cubic centimeters per hour (1.5 liters per minute) or higher. Most existing infusion pumps are designed for medication delivery and are limited in their performance to the routine range of infusion rates. Such pumps are not capable of rapid intravenous infusion. Although some prior infusion systems can deliver rapid infusion, those prior rapid infusion devices are physically large, complex systems that require dedicated operation by skilled technicians. For example, U.S. Pat. No. 6,942,637 issued to Cartledge et al. describes a rapid infusion system having a differential drive that interacts with multiple motors to achieve the variable pumping rates desired. U.S. Pat. No. 6,942,637 specifically describes a differential drive that includes, among other components, multiple motors, such as a high speed motor and a stepper motor, and a combination of gears mechanically linking the multiple motors to a common drive shaft.

In other uses, a fluid pump system may be used for fluid delivery during certain surgical procedures, such as arthroscopic surgeries, to distend the area of operation. For example, saline solution is infused into the joint during an arthroscopy to expand the joint and clear the surgical field of view. However, current technologies are deficient in allowing the control of both the pressure and temperature of the fluid so as to not cause excessive cooling or warming of the area.

Accordingly, what is needed is a pump device for variably controlling fluid flow rates, fluid flow pressures, and fluid temperatures that is compact and easily operated by medical personnel in the course of their other duties. What is also needed is a low-to-high speed pump device that may heat or cool fluid efficiently and safely, that utilizes a sterile, disposable fluid containment system that can be readily attached and removed from a separate pumping mechanism.

SUMMARY OF THE INVENTION

Described is a system for controlling the flow and temperature of a fluid being infused into a patient's body while the infusion is taking place. Such a pump system is also referred to as an, an infusion system, or an in-line heating or cooling infusion system. The system also provides for improved monitoring of air in the infusion system such to prevent the introduction of air into the patient's body receiving the fluid infusion. The pump system also provides variable flow rates and flow pressures that may be dynamically controlled by way of an electronically controlled motor, that serve a vast amount of infusion needs. The pump system may also be controlled through a simple user interface to a system having stored logic and data collection capabilities that allows for simple and accurate control of the system. Improved heat exchange efficiencies through advantageous construction and circuitry of the system components are also provided for while also reducing the risk of sustaining electric shock by the patient. The components of the disposable cartridge align with their respective component mates on the pump housing, so as to make attaching the disposable cartridge to the pump housing and operation simple and effective.

More specifically, a pump system having simple control of prime and infusion operation may include a pump housing and a cartridge removably coupled to the pump housing. The pump housing may include a motor driven pump, a prime input, an infusion input, and a central controller. The cartridge may include at least one infusion tubing. The central controller may cause the motor driven pump to pump fluid through the infusion tubing and the cartridge to remove air from the infusion tubing in response to a user's selection of the prime input. The central controller may also cause the motor driven pump to pump fluid through the infusion tubing and the cartridge to a patient at a predetermined flow rate or a predetermined flow pressure in response to selecting the infusion input.

In another example, a pump system provides for accurate and responsive temperature control. The pump housing of this system includes a motor driven pump, a thermal element, a heat exchanger temperature sensor, at least one user input control, and a central controller. The cartridge includes a heat exchanger that is correspondingly aligned with the thermal element. The heat exchanger temperature sensor senses the temperature of the heat exchanger on the cartridge and communicates the sensed temperature to the central controller. In response, the central controller can adjust the thermal element to maintain an approximately constant first temperature of the heat exchanger.

Additionally a method for cooling the temperature of a region of a patient's body is provided for. The method includes cooling fluid to a lower temperature by a pump system having a cooling element as described, and delivering the fluid to the patient after substantially reaching the lower temperature.

In another example, a pump system that allows selectably and accurately controlling flow pressure is provided for. A pump system may include a pump housing and a cartridge removably coupled to the pump housing. The pump housing includes a motor driven pump, at least one user input control, a central controller, and an electronic controller at least partially controlling the motor driven pump. A pressure sensor in the cartridge may sense the pressure of a fluid passing through infusion tubing in the cartridge, and communicate the sensed pressure to the central controller. In response, the central controller may cause the electronic controller to adjust the motor driven pump so as to maintain an approximately constant pressure of the fluid passing through the infusion tubing. Additionally, a method described herein provides for controlling the pressure of fluid during delivery to a patient to an approximately constant pressure.

BRIEF DESCRIPTION OF THE DRAWINGS

FIG. 5a shows an exploded view of an exemplary heating element in accordance with an example of the present invention.

DETAILED DESCRIPTION OF THE INVENTION

Figure 1:
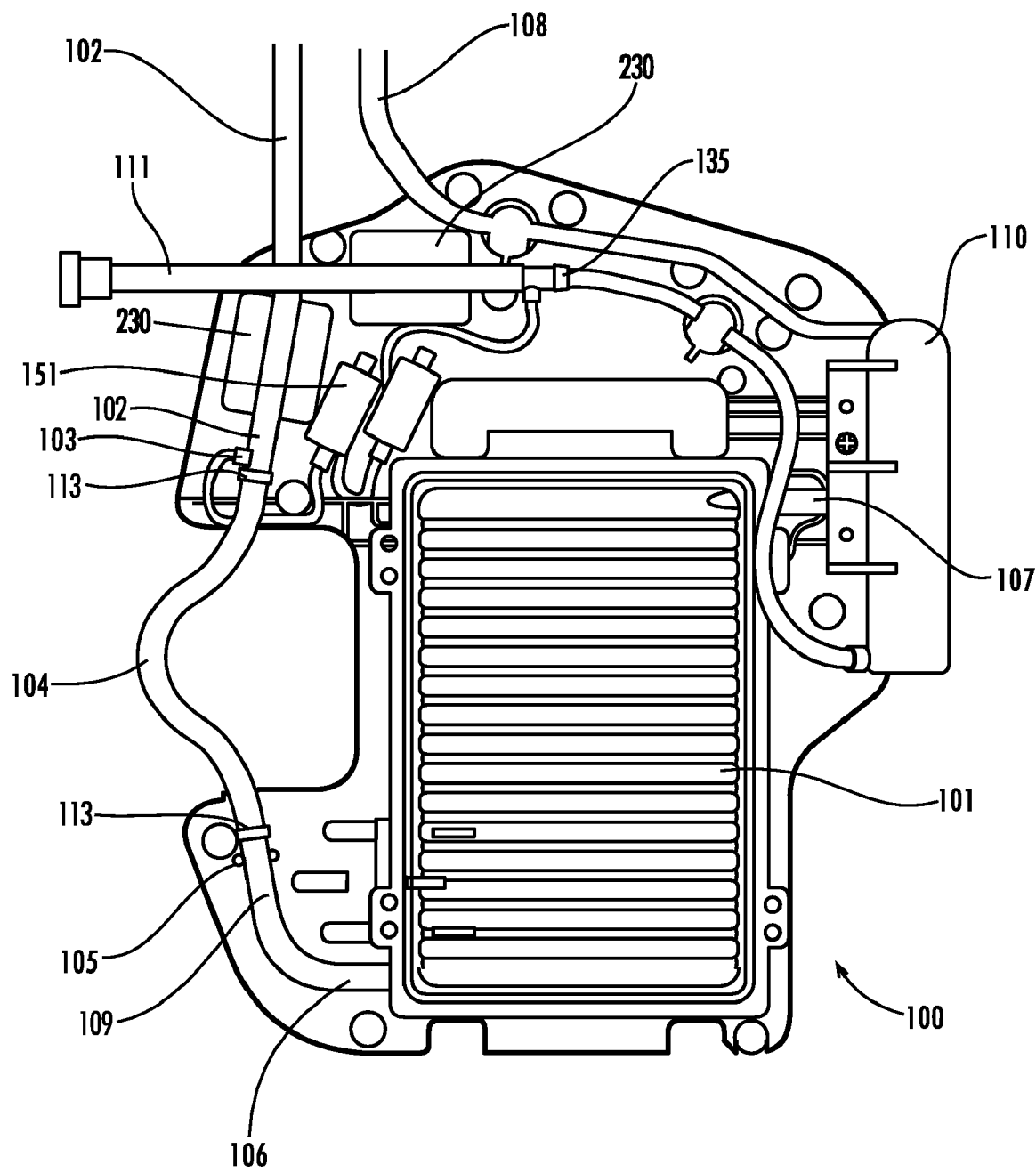
FIG. 1 is an elevation view of the internal elements of a disposable cartridge in accordance with an example of the present invention.

A disposable heat exchange cartridge and pump device for use during fluid infusion into a patient's body is described. The disposable heat exchange cartridge is removably coupled to an infusion pump device which provides not only the energy or power required to heat or cool the fluid being infused, but also provides, the flow generating pump and mechanisms for monitoring and regulating particular aspects of the fluid pumping system. More specifically, the disposable heat exchange cartridge may include a heating element disposed in the pump device by means that increase the efficient transfer of heat energy, while also providing safe and simple operation of the system. Alternatively, the disposable heat exchange cartridge may include a cooling element similarly disposed to cool the temperature of the fluid. Additionally, the disposable heat exchange cartridge has components that are advantageously aligned with their respective component mates on the pump system, allowing for simple attachment and detachment. Furthermore, the pump device includes a simple user interface that allows for accurate control of the pump device and the collection of operation-related data. In this description of the invention, reference will be made to the embodiments shown in FIGS. 1-16 wherein like numerals are used to designate like parts throughout. FIGS. 2a-2d describe a currently preferred embodiment of the present invention and should not be viewed as limiting.

One aspect described herein is a pump system that includes a pump housing and a cartridge removably coupled to the pump housing. The pump housing includes a motor driven pump, a prime input, an infusion input, and a central controller in communication with the prime input, the infusion input, and the motor driven pump. The cartridge includes at least one infusion tubing. The central controller is configured to cause the motor driven pump to pump fluid through the infusion tubing and the cartridge to remove air from the infusion tubing in response to the selection of the prime input. The central controller is further configured to cause the motor driven pump to pump fluid through the infusion tubing and the cartridge to a patient at a predetermined flow rate or a predetermined flow pressure in response to the selection of the infusion input.

In one embodiment, the cartridge may include a first infusion tubing, a second infusion tubing, an air output tubing, and an air-trap communicating with the first infusion tubing, the second infusion tubing, and the air output tubing. The first infusion tubing carries fluid to the air-trap, the second tubing caries fluid out of the air-trap, and the air output tubing allows air to exit the air-trap. The pump housing may further include a fluid outflow flow limiting mechanism that reversibly restricts the flow of fluid through the second infusion tubing and an air output flow limiting mechanism that reversibly restricts the flow of air through the air output tubing. The central controller may cause the fluid outflow flow limiting mechanism to restrict the flow of fluid through the second infusion tubing and cause the air output flow limiting mechanism to allow the flow of air through the air output tubing in response to the selection of the prime input. In one embodiment the fluid outflow flow limiting mechanism and the air output flow limiting mechanism may be pinch clamps that operably and reversibly engage and compress the second infusion tubing and the air output tubing, respectively, when actuated so as to prevent the flow of fluid or air at the points of compression.

In one embodiment described herein, the central controller may execute manual priming of the pump system by causing the motor driven pump to begin pumping fluid at a predetermined rate into the air-trap to remove air from the first infusion tubing while the prime input is depressed and to stop the pumping fluid when the prime input is released. The predetermined rate may be between about 100 milliliters per minute to about 1200 milliliters per minute.

The pump housing may further include a lower level sensor and an upper level sensor in communication with the central controller. The lower level sensor and the upper level sensor may detect fluid at a first point and a second point in the air-trap, respectively, wherein the first point is positioned distal to the second point in the air-trap. In this embodiment the central control may execute automatic priming in response to depressing and releasing the prime input by causing: the motor driven pump to pump fluid at a first predetermined rate into the air-trap to force air out of the air output tubing, the motor driven pump to increase pumping to a second predetermined rate when the fluid is detected by the lower level sensor, and the motor driven pump to stop pumping after a predetermined volume of the fluid is pumped subsequent to detection by the lower level sensor. The first predetermined rate may be between about 10 milliliters per minute to about 900 milliliters per minute and the second predetermined rate may be between about 900 milliliters per minute to about 1200 milliliters per minute.

In one embodiment described herein, the pump system may further include a plurality of input buttons that cause at least one of manual priming, automatic priming, heating, pressure adjustment, infusion rate adjustment, start pump operation, or stop pump operation in response to the selection thereof. In response to a single selection of one of the plurality of input buttons, the pump system may adjust one of infusion mode, infusion rate, maximum pressure setting, or heater setting. Further, the pump system may be configured to operate in one of standard infusion mode, rapid infusion mode, or bolus infusion mode in response to the selection of one of a standard infusion input button, rapid infusion input button, or a plurality of bolus preset input buttons, respectively. Additionally, the plurality of bolus preset input buttons may include a first button that causes delivery of a first volume when selected and a second button that causes delivery of a second volume when selected. The standard infusion mode and the rapid infusion mode may pump fluid at a first predetermined flow rate and at a second predetermined flow rate, respectively, wherein these rates may be adjustable. Further, the central controller may be configured to cause an increment in the flow rate in response to the selection of a rate increase input button and causes an decrement in the flow rate in response to the selection of a rate decrease input button, wherein the increments and decrements are between about 1 milliliter per hour and about 50 milliliters per minute. Additionally, the central controller may be configured to cause a rapid increment in the flow rate in response to continually depressing the rate increase input button and causes a rapid decrement in the flow rate in response to continually depressing the rate decrease input button, wherein the rapid increments and decrements are between about 10 milliliters per minute and about 500 milliliters per minute. Any of the adjusting may occur prior to or during operation of the pump system.

One aspect described herein is a pump system that includes a pump housing and a cartridge removably coupled to the pump housing. The pump housing includes a motor driven pump, a thermal element, a heat exchanger temperature sensor, at least one user input control, and a central controller in communication with the user input control or controls, the motor driven pump, the thermal element, and the heat exchanger temperature sensor. The cartridge includes a heat exchanger that is correspondingly aligned with the thermal element. The heat exchanger temperature sensor senses the temperature of the heat exchanger on the cartridge and communicates the sensed temperature to the central controller. In response to the selection of the at least one user input control, the central controller adjusts the thermal element in response to the sensed temperature to maintain an approximately constant first temperature of the heat exchanger.

In one embodiment, the thermal element is a heating element, and the pump system includes a heat input control. In response to the selection of the heat input control the central controller may adjust the heating element to maintain the first temperature greater than the temperature of fluid being delivered to the cartridge. The first temperature maintained may be between about 35° Celsius and about 50° Celsius, and in some embodiments between about 37° Celsius and about 43° Celsius. The central controller may be configured to cause the heating element to stop producing heat when the heat exchanger temperature sensor senses a pre-defined temperature, which may be defined as greater than the first temperature. Further, the central controller may be configured to cause the pump system to stop delivering fluid to a patient when the heat exchanger temperature sensor senses a pre-defined temperature, which may be defined as greater than the first temperature. The two pre-defined temperatures may be the same or different temperatures.

In another embodiment described herein, the thermal element of the pump housing may be a cooling element and the pump system may include a cooling input control. In response to the selection of the cooling input control, the central controller adjusts the cooling element to maintain the first temperature less than the temperature of fluid being delivered to the cartridge. In this embodiment, the first temperature maintained may be between about 0° Celsius and about 37° Celsius, and between about 40° Celsius and about 25° Celsius in some embodiments. In this embodiment the central controller may be configured to cause the cooling element to stop cooling when the heat exchanger temperature sensor senses a pre-defined temperature, which may be lower than the first temperature. Further, the central controller may be configured to cause the pump system to stop delivering fluid to a patient when the heat exchanger temperature sensor senses a pre-defined temperature, which may be lower than the first temperature.

In one embodiment described herein, the pump housing may further include a fluid outflow flow limiting mechanism positioned to reversibly prevent fluid from flowing out of the cartridge and to a patient and the cartridge may further include an infusion tubing. In this embodiment, the central controller may be configured to cause the fluid outflow flow limiting mechanism to reversibly engage the infusion tubing to prevent fluid from flowing to the patient in response to the heat exchanger temperature sensor sensing one of the pre-defined temperatures described.

In one embodiment, the central controller may adjust the thermal element in response to the fluid flow rate detected by the central controller. The speed by which the central controller adjusts the thermal element may be directly proportional to the fluid flow rate. Additionally, the pump housing may further include an inflow temperature sensor in communication with an infusion tubing that senses the temperature of fluid before entering the heat exchanger, whereby the central controller can adjust the thermal element in response to the temperature of fluid sensed by the inflow temperature sensor. The speed by which the central controller adjusts the thermal element may be directly proportional to the difference between the temperature of the fluid sensed by the inflow temperature sensor and a target temperature. Further, in some embodiments, the central controller can adjust the thermal element in response to at least one of the fluid flow rate determined by the central controller, the temperature of fluid sensed by the inflow temperature sensor, or the heat exchanger temperature sensed by the heat exchanger temperature sensor.

One aspect described herein is a method for cooling the temperature of a region of a patient's body. The method includes the steps of providing fluid at a first temperature to a cartridge having a cooling element as described herein, selecting at least one user input control of the pump system, cooling the fluid to a second temperature lower than the first temperature by the cooling element of the pump system in response to the selection of the user input control, and delivering the fluid to the patient after substantially reaching the second temperature. In one embodiment the second temperature may be between about 0° Celsius and about 37° Celsius, or between about 4° Celsius and about 25° Celsius in other embodiments.

In one embodiment described herein, the method is practiced when infusing saline into the patient's bladder to lower the patient's core body temperature to a third temperature. In this embodiment, the method may further include the step of draining the saline from the patient's bladder while continuously delivering new volumes of cooled the saline until the patient's core temperature reaches the third temperature, which may be between about 0° Celsius and about 37° Celsius.

In another embodiment the method is practiced when intravenously infusing blood to the region of the patient's body to cool the region to a third temperature. This method may include intravenously infusing blood to the patient's brain region or to the patient's heart region. The third temperature may be between about 0° Celsius and about 37° Celsius.

One aspect described herein is a pump system that includes a pump housing and a cartridge removably coupled to the pump housing. The pump housing includes a motor driven pump, at least one user input control, a central controller in communication with the at least one user input control and the motor driven pump, and an electronic controller in communication with and at least partially controlling the motor driven pump and in communication with the central controller. The cartridge includes an infusion tubing and a pressure sensor. The pressure sensor senses the pressure of a fluid passing through the infusion tubing and communicates the sensed pressure to the central controller. In response to the selection of the at least one user input control, the central controller causes the electronic controller to adjust the motor driven pump in response to the sensed pressure to maintain an approximately constant pressure of the fluid passing through the infusion tubing. In one embodiment, the pressure sensor may be an outflow pressure sensor and the user input controls may include at least one of a pressure increase input, a pressure decrease input, a maximum pressure input, or a preset pressure input. In this embodiment the approximately constant pressure may be between about 0 mmHg and about 750 mmHg.

One aspect described herein is a method for controlling the pressure of fluid that includes the steps of providing the fluid to a cartridge of a pump system as described herein, selecting at least one user input control of the pump system, and delivering the fluid to a patient at an approximately constant pressure, in response to the selection of the user input control. The fluid may be delivered to the patient at a pressure between about 0 mmHg and about 750 mmHg, or between about 25 mmHg and about 150 mmHg in some embodiments. In this embodiment the user input controls include at least a pressure increase input, a pressure decrease input, a maximum pressure input, or a preset pressure input. In one embodiment this method is practiced when delivering the fluid to a patient during an arthroscopic procedure.

In one embodiment, a heat exchanger 101, as depicted in FIG. 1, is contained within a disposable cartridge 100. The disposable cartridge 100 is removably attached to a pump system such that once the treatment is completed, the disposable cartridge 100 can be removed and discarded. The disposable cartridge 100 is self-contained and, once attached to the pump system, need not be adjusted or manipulated. Fluid enters the disposable cartridge 100 in the primary inflow tube 102, which draws fluid from the fluid source. The fluid is drawn into the primary inflow tube 102 and flows past an inflow bubble detector 120, which is further described in reference to FIG. 2d. The inflow bubble detector 120 may be an ultrasonic sensor that sends a signal across the inflow tube 102. In other embodiments, the bubble detector 120 may be an optical-based sensor, such as a laser sensor, or the like, as is known in the art, to detect a change in the fluid properties, and thus the presence of bubbles. Attenuation in the signal reaching a certain predetermined level, indicating no fluid in the system, may cause the system to Stop pumping. After the fluid flows past the inflow bubble detector 120, the temperature is sensed by the inflow temperature sensor 260, which is further described in reference to FIG. 2d. The inflow temperature sensor 260 may be an infrared temperature sensor. In other embodiments, the inflow temperature sensor 260 may be an optical temperature sensor, such as a laser sensor, a thermistor, or the like, as is known in the art. The inflow bubble detector and inflow temperature sensor may be integrated with the pump housing and align with one of at least two detector interfaces 230 on the disposable cartridge and communicate with the primary inflow tube, as is described in reference to FIG. 2d. The inflow temperature sensor 260 may provide the fluid temperature, before entering the heat exchanger, as an input to a central controller to allow for more accurate control of heating or cooling elements, described further herein. Next, the fluid proceeds past a first t-junction, which serves as the inflow pressure junction 103. The inflow pressure junction 103 is in fluid communication with a first air chamber 151. The inflow pressure junction 103 and the first air chamber 151 communicate with pressure sensors on the pump housing to determine the pressure of the fluid flow as it enters the pump loop 104 to allow for proper regulation of the fluid flow. The pump loop 104 interacts with a pump device, as described in reference to FIG. 10. The pump loop 104, when interacting with a pumping system, pushes the fluid through the remainder of the disposable cartridge 100. When the fluid leaves the pump loop 104 it flows through a second t-junction, which serves as the pump outflow pressure junction 105. The pump outflow pressure junction 105 and another air chamber may communicate with sensors on the pump device to determine the pressure of the fluid as it exits the pump loop 104, so that the pressure of the fluid through the disposable cartridge 100 can be regulated. In one embodiment, the pump loop 104 may be a different tube coupled to the primary inflow tube 102 and a pump outflow tube 109 and securely affixed to the disposable cartridge 100.

Figure 2A:
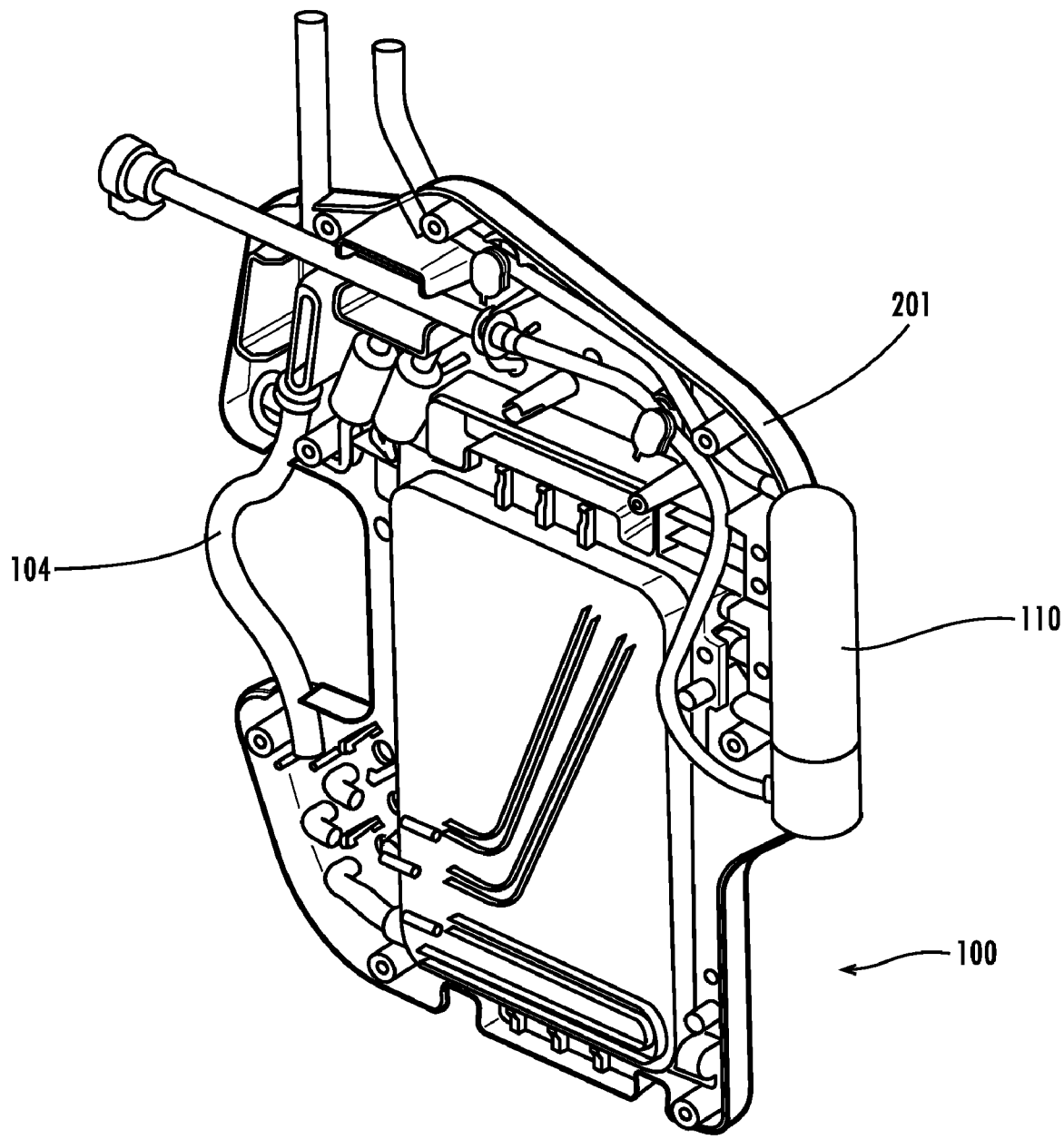
FIG. 2a shows a different orientation of the disposable cartridge in accordance with an example of the present invention (near cover of disposable removed).
Figure 2B:
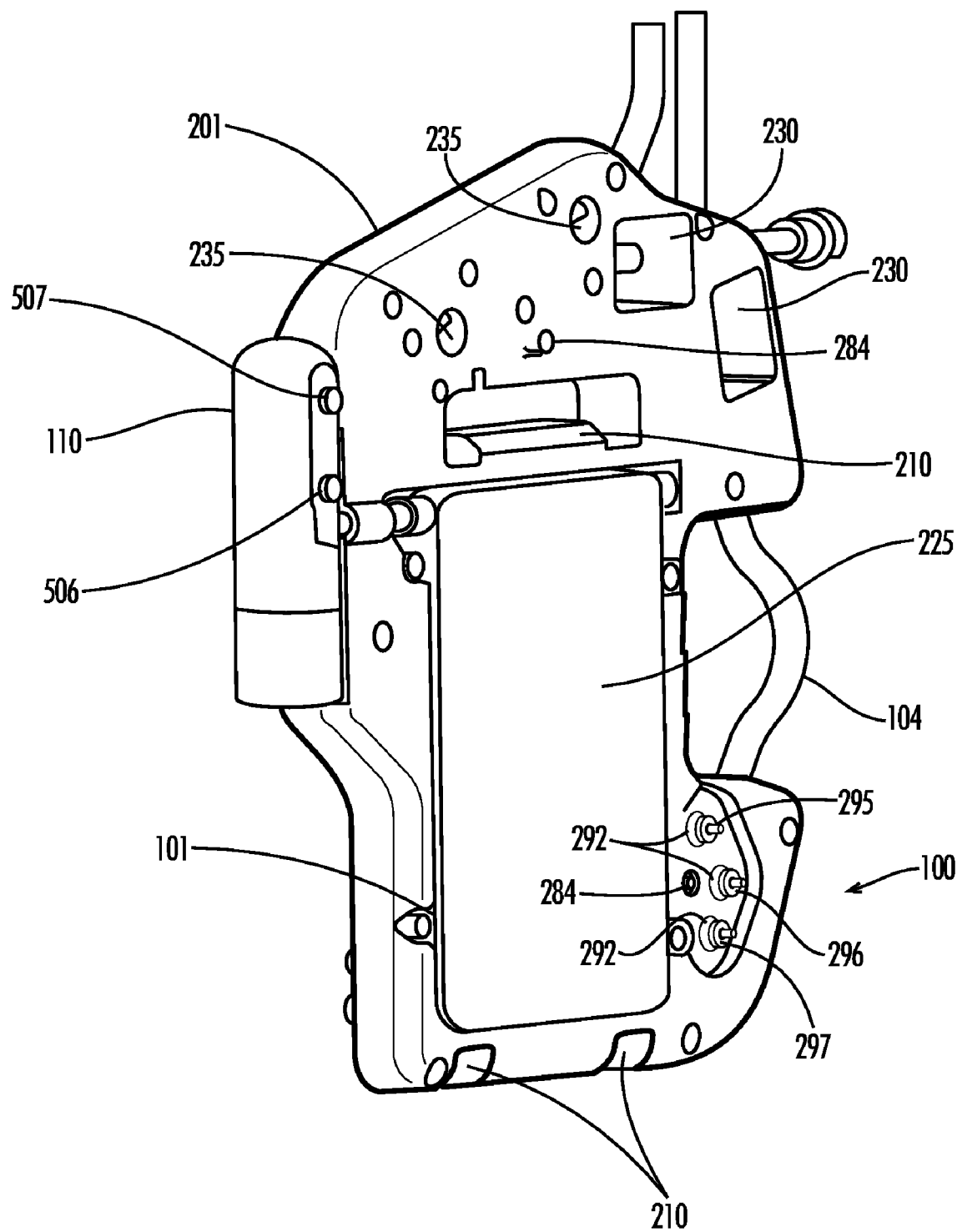
FIG. 2b shows the side of the disposable cartridge of an example of the present invention which abuts the pump housing.

The fluid then passes into the heat exchanger 101 via the exchanger inlet port 106 at the lower aspect of the heat exchanger. In the above described embodiment including a pump outflow tube 109, the pump outflow tube 109 couples with the exchanger inlet port 106 of the heat exchanger. After the fluid passes through the turbulent environment established by the heat exchanger 101, it exits via the exchanger outlet port 107 located at a position opposite the exchanger inlet port 106 at the upper aspect of the heat exchanger 101. At this point, the fluid for infusion has undergone its warming or cooling and the desired temperature has been reached. A heat exchanger temperature sensor 287, as described in reference to FIG. 2d, is positioned on the pump housing and communicates with the heat exchanger 101 to sense the temperature of the heat exchanger, and thus a relative temperature of the fluid contained therein. In an alternative embodiment, a temperature sensor may also be placed internally within the heat exchanger 101 so as to be in direct contact with the fluid contained therein. In a manner similar to that of the inflow temperature sensor 260 described above, the heat exchanger temperature sensor 287 may provide the heat exchanger temperature as an input to the central controller for controlling the operation of the heating or cooling elements. For example, if the heat exchanger temperature sensor senses a temperature greater or lower than a predetermined maximum, for example 45° Celsius when heating, the central controller may limit or stop power to the heating or cooling element and may cause the infusion device to stop pumping fluid to the patient. The heat exchanger temperature sensor 287, or the temperature sensor positioned internally within the heat exchanger just described, may be a contact thermocouple, or the like, as is known in the art.

The fluid exits the heat exchanger 101 via the exchanger outlet port 107, and then enters the air-trap 110 at about the mid-point along the long-axis of the air-trap 110. Fluid flows out of the air-trap 110 and through a third t-junction, which serves as the fluid outflow pressure junction 135. Similar to the inflow pressure junction and pump outflow pressure junction, the fluid outflow pressure junction 135 and another air chamber may communicate with sensors on the pump device to measure the pressure of the infusion fluid prior to delivery to the patient. The fluid outflow pressure junction 135 assists in allowing for the control of the infusion pressure so pressure can either be substantially maintained at a pre-defined pressure, or kept within a pre-defined maximum or minimum limit. Next, prior to delivery to the patient, the fluid is sensed by the outflow bubble detector 112 and subsequently the outflow temperature sensor 261, aligning with another bubble detector interface 230, in the same manner as is described for the inflow bubble detector and inflow temperature sensor, described above and further in reference to FIG. 2d. The outflow bubble detector 112 determines whether excess amounts of air have infiltrated the system. If an unacceptable level of air remains in the fluid as it flows past the outflow bubble detector 112, the system may not allow infusion of the fluid into the patient's body. If the fluid contains no air, or a minimal amount of air such to be acceptable, the fluid passes the outflow bubble detector 112 and into the patient via the primary outflow tube 111. The outflow temperature sensor 261 measures, for example, using an infrared sensor as is known in the art, the temperature of the infusion fluid prior to delivery to the patient. Thus, if the fluid temperature exceeds pre-defined limits, the outflow temperature sensor 261 can signal to the device to stop pumping and subsequently alter the heating controls, or alternatively stop the device entirely. In other embodiments, the outflow temperature sensor 261 may be an optical temperature sensor, such as a laser sensor, a thermistor, or the like, as is currently known in the art.

Figure 3:
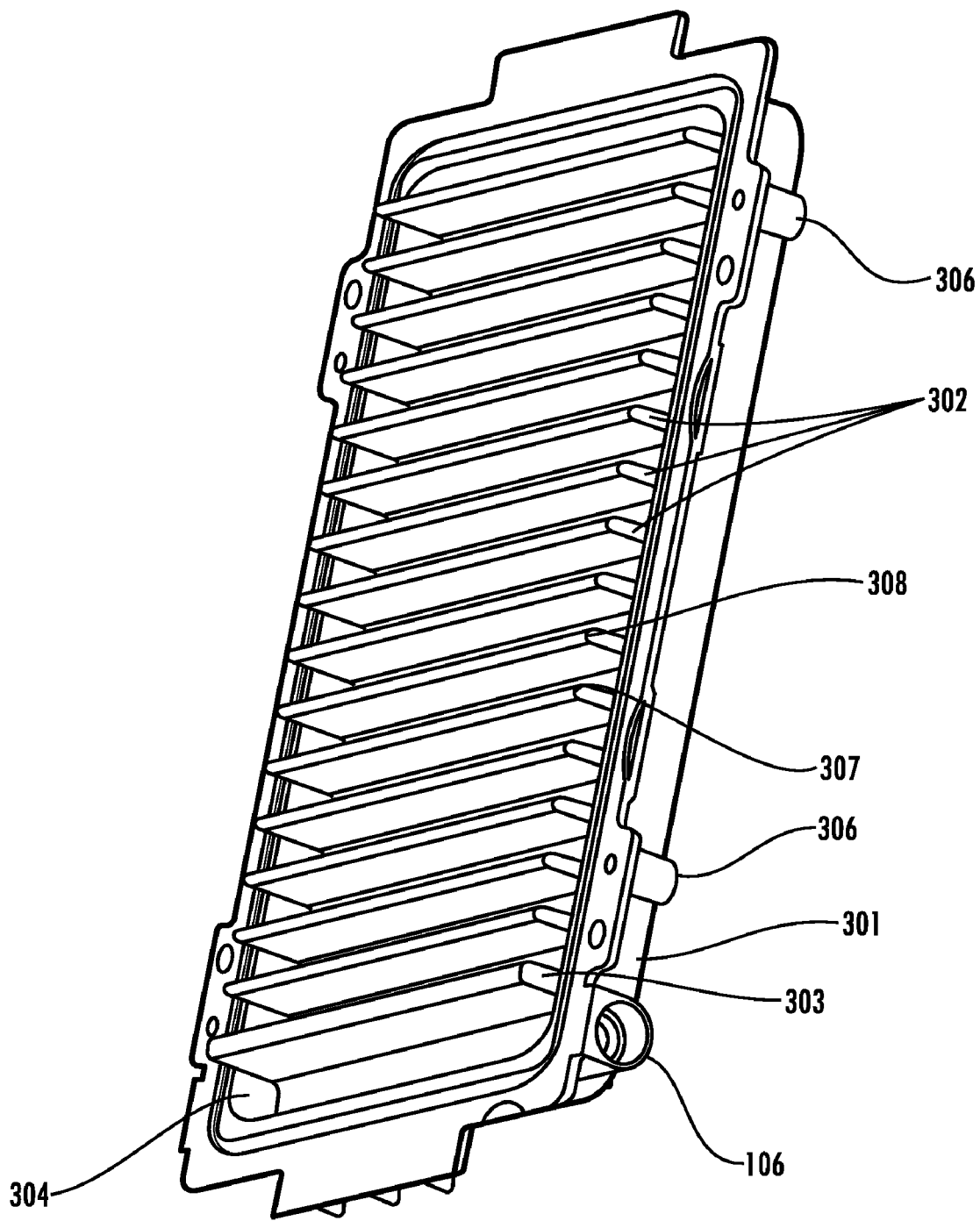
FIG. 3 shows one-half of the heat exchanger—one plurality of fins—in accordance with an example of the present invention.
Figure 4:
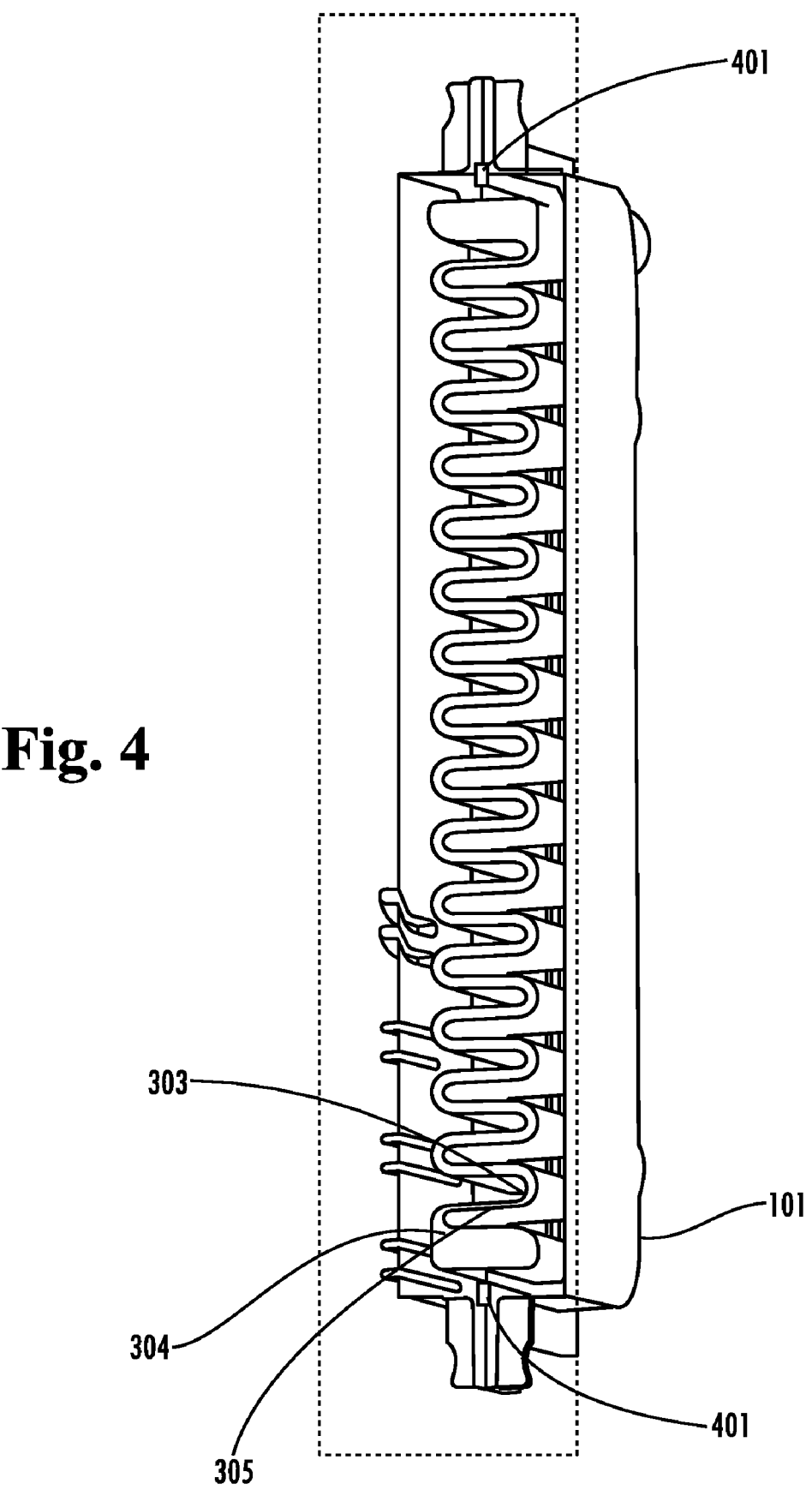
FIG. 4 shows a cross-section of the heat exchanger, artificially hollowed, showing a fluid flow path in accordance with an example of the present invention.

A detailed description of the heat exchanger 101 requires reference to FIGS. 3 and 4. Heat exchanger 101 can be created by two halves cast from the same mold, each containing a plurality of fins. A first half 301 is comprised of the exchanger inlet port 106 and a plurality of fins comprising a series of spaced fins 302. With the exception of a specially sized flow fin 303, each of the fins 302 are of equal size and are spaced equidistant from one another. As fluid enters the heat exchanger 101 through the exchanger inlet port 106, the fluid fills the flow cavity 304 defined by the inner walls of the heat exchanger and the flow fin 303. When in operation, the heat exchanger is oriented such that a lower aspect, where the inlet port 106 is located, and an upper aspect, where the outlet port is located, are oriented in a vertical form, forcing fluid to flow in an upwardly direction through the heat exchanger and against gravitational forces. Because of the special shape given the flow fin 303, the fluid fills the flow cavity 304 before proceeding up through the heat exchanger 101. An alternate embodiment of the heat exchanger 101 may be constructed from two dissimilar halves, where the half farthest from the heating or cooling element has a greater mass. Similarly, in an embodiment having dissimilar halves, any number of fins 302 may be included having any spacing therebetween, because symmetry is not required. Though, it is appreciated that the first embodiment, having symmetrical halves constructed from the same mold, is the preferred embodiment considering manufacturing costs.

Using FIG. 4 to describe the flow of fluid through the heat exchanger 101, fluid enters the flow cavity 304 via the exchanger inlet port. Because of the differentially sized flow fin 303, fluid preferably first fills the flow cavity 304 before rising over the first fin. This preliminary filling allows the fluid to fill the width of the heat exchanger and flow as a wide ribbon of fluid across the fins—opposed to a laminar flow through a long but narrow conduit. The flow fin 303 accomplishes the appropriate spreading of fluid by creating a thinner flow gap 305 between the flow fin 303 and the first of the plurality of fins of regular shape. The fluid then flows up the length of the heat exchanger 101 between the exchanger inlet port and the exchanger outlet port. As the fluid rises, it travels in wave form as a shallow, but wide, ribbon of fluid. The wide-flow, short linear track flow pattern created by the heat exchanger, creates a turbulent flow causing increased molecular circulation within the fluid. While laminar flow within typical conduits, such as tubes, see higher molecular "turnover" in the central portion of the conduit, the turbulent flow within the heat exchanger 101 provides much more exposure of different molecules to the interior surface of the heat exchanger thereby facilitating more efficient and effective energy transfer.

It is appreciated that in other embodiments the heat exchanger 101 may be constructed so as to cause a discrete flow path, rather than a disruptive, laminar flow path, as previously described. For example, a heat exchanger configured in this manner may not have fins, but instead may provide a distinct path by a series of flow walls, for example, in a serpentine-type flow path, so as to increase exposure of the fluid to the thermally conductive heat exchanger. It is further appreciated that other means of directing flow through a heat exchanger, so as to efficiently facilitate heat transfer, as are known in the art, may be employed.

Returning to FIG. 3, the other half of the heat exchanger can be created from the same mold, wherein the exchanger inlet port 106, becomes the exchanger outlet port. Once formed, the two halves are mounted together, using means known in the art, including, but not limited to, bolts, screws, or other mechanical means, as well as glues, cements, or other chemical means. If mechanical means are used, then fixation tabs 306 can be used to house the fixation devices.

A further benefit achieved by creating the heat exchanger 101 from the same mold is that all surface areas in which the infusion fluid contacts will be the same highly conductive material, such as anodized aluminum, as further described below. Rather than creating only the half of the heat exchanger 101 that will communicate with the heating element of the pump housing made from highly conductive material and creating the outer half of the heat exchanger 101 from an insulative material, as one might intuit would reduce temperature loss, also creating the outer half from highly conductive material, provides further surface area and greater mass to transfer heat from the heating element or to the cooling element of the pump housing, through the heat exchanger 101, and to or from the infusion fluid. Thus, as the heating element transfers heat to the heat exchanger 101, heat is dissipated to the plurality of fins 302 from both the interior half and the outer half. Similarly, the cooling element may cool the heat exchanger by cooling the plurality of fins 302 by cooling the two halves.

FIG. 4, the cross-section view of the heat exchanger further shows the seal seat 401, which provides for a space to place a seal about the circumference of the heat exchanger to increase the liquid impermeability of the heat exchanger, such as an o-ring. It should be noted that while the heat exchanger of the present embodiment is described as being formed from two identical halves, the heat exchanger could be formed as a singular piece, or more than two pieces, and from more than one asymmetric mold. For ease in manufacture, however, two identical halves, as described herein, allows for the proper result through less cost.

The heat exchanger of the present invention can be formed from any number of thermally conductive materials, such as: cast anodized aluminum, copper, gold, silver, carbon foam, ceramics, and the like, as is known in the art. The material chosen for use in the heat exchanger of the present invention must be capable of adequate heat conduction and dispersion to ensure proper heat distribution across the surface, as well as heat transfer to or from the fluid desired to be warmed or cooled. Thermodynamics dictates that for two materials with the same specific heat, that is the amount of heat energy required to change the temperature of the material one unit per unit of mass, the material with a greater mass will more efficiently transfer heat to the material with a lesser mass. This efficiency level is often understood as thermal capacitance—in that materials with greater thermal capacitance (i.e. mass) will retain more heat while transferring energy to the adjacent material, sufficient to greatly increase the temperature of the second material, without the unwanted loss of energy. Analogizing the heat exchange occurring between the heat exchanger and the infusion fluid to be warmed by way of example, a material with a mass of 1.5 kilograms is heated to 60° Celsius and placed in close, direct contact with a material having a mass of 0.5 kilograms at a temperature of 40° Celsius. When the heating is complete, both materials will achieve a temperature of 55° Celsius. The energy stored by the hotter component, via its increased mass, allows for a better exchange of heat energy between the two materials. The converse is also true, by which the component with the increased mass is cooled. The selection of a material, given the special requirements of the present invention, therefore requires the consideration of the mass of the material, as well as the thermodynamic properties of that material.

Figure 5:
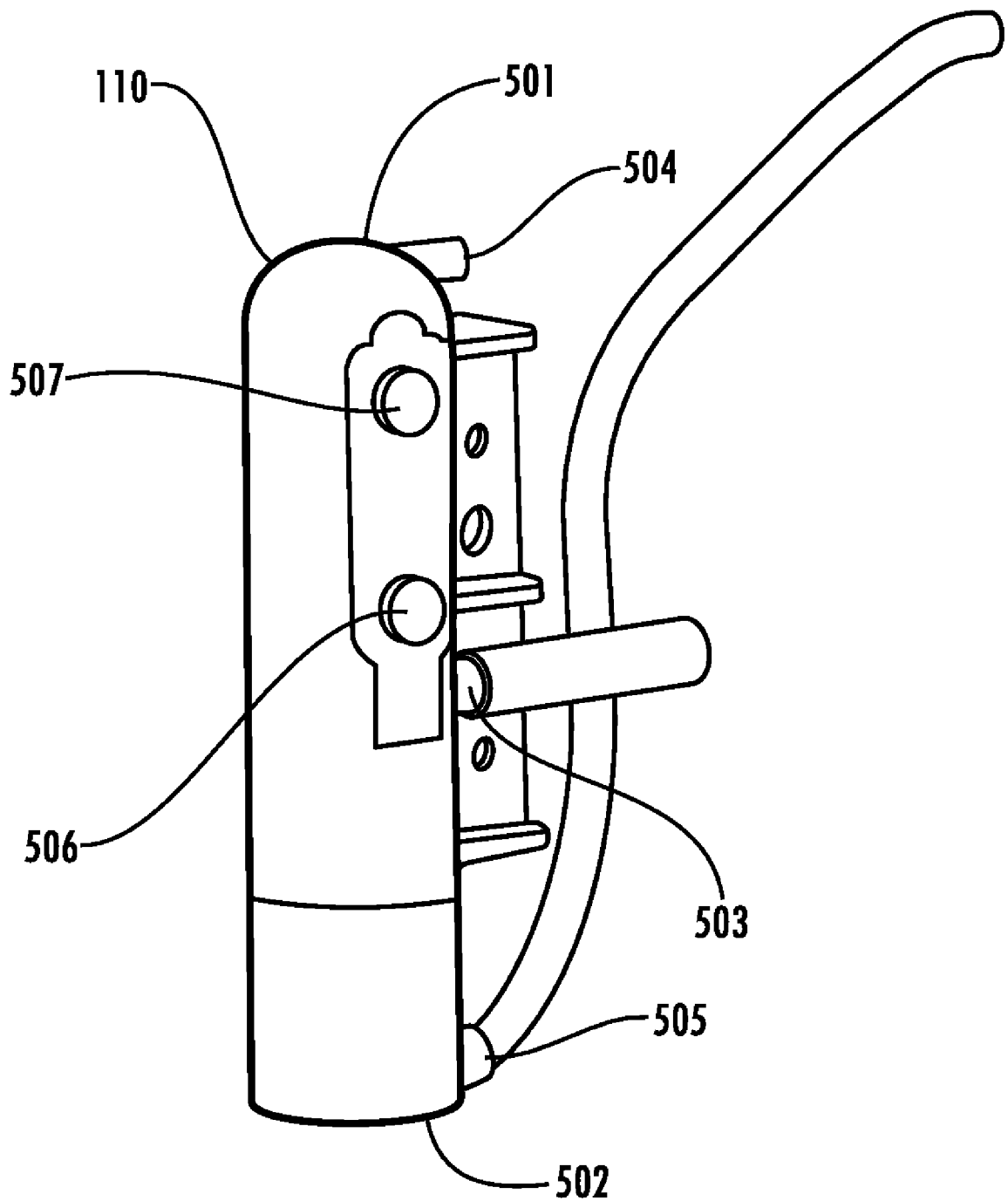
FIG. 5 shows an outside view of an air-trap in accordance with an example of the present invention.

FIG. 5 shows an enlarged view of the air-trap 110 and its connective conduits. While the air-trap is described with reference to specific shapes, it should be apparent to one of skill in the art that any shape which would allow for the reversal of fluid flow direction at the fluid output port of the air-trap will allow for the monitoring and removal of air from the cartridge system. The air-trap 110 is generally cylindrical in shape with a domed top 501 and flattened bottom 502. Fluid enters the air-trap 110 at the air-trap intake port 503, located at approximately midway along the long axis of the air-trap. Fluid enters the air-trap 110 from the heat exchanger in order to remove any air trapped or introduced into the fluid. The air to be removed may have come from failure to purge the fluid source of air before introducing it to the present invention. It is also possible that the heating of the fluid causes the release of bound gas, creating bubbles, which, if allowed to enter the patient's body, could be deleterious or even deadly. Fluid exits the air-trap 110 through the fluid output port 505 located at the bottom 502 of the air-trap.

Figure 6:
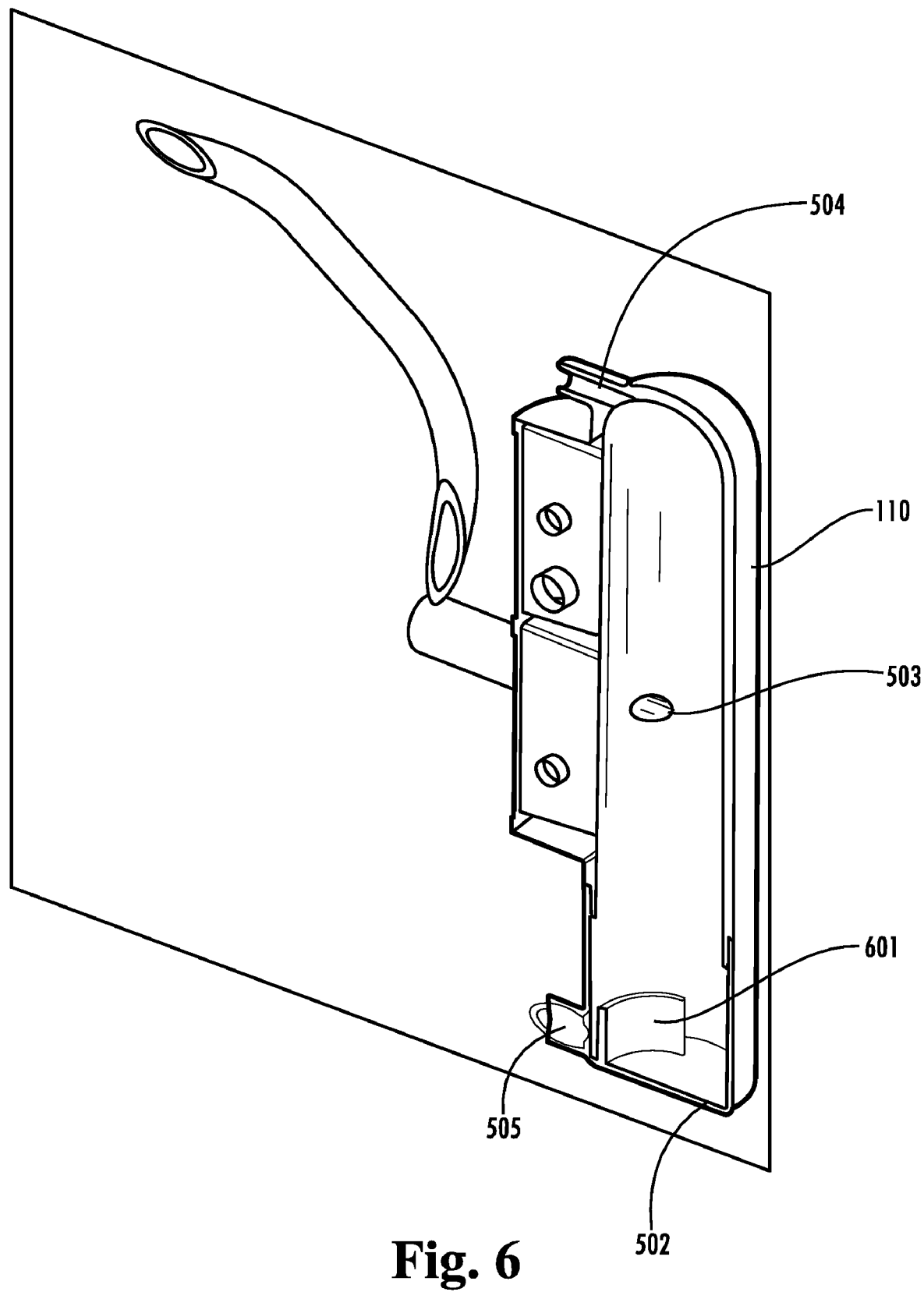
FIG. 6 shows a cross-section of an air-trap in accordance with an example of the present invention.

FIG. 6 depicts a cross-section of the air-trap 110. In this view, one can see the air-trap intake port 503 as it interfaces with the air-trap 110. The air-trap intake port 503 is smoothed to the inside wall of the air-trap and is positioned off of the mid-line of the long axis of the air-trap. This position of the air-trap intake port 503, relative to the mid-line of the long axis of the air-trap, causes the fluid being introduced to the air-trap to flow about the cylindrical form of the air-trap in a clockwise direction as the fluid fills and continues to enter the air-trap. This flow pattern creates a vortex within the air-trap, pulling air downward toward the fluid output port 505. At the bottom 502 of the air-trap there is located a flow disrupter 601, which is positioned adjacent to the fluid output port 505. The flow disrupter 601 can extend from the inner wall of the air-trap or the inner wall of the bottom 502 of the air-trap. As the fluid, which is traveling clockwise about the air-trap, flows across the flow disrupter 601, a differential in pressure at the fluid output port 505 is created, drawing the liquid out of the air-trap and allowing the air or gas bubbles to flow upward along the long-axis of the air-trap.

Returning to FIG. 5, the level of fluid within the air-trap 110 is continuously monitored while the infusion device is being operated. The air-trap 110 includes one or more sensor interfaces for communication with one or more sensors on the pump housing. For example, the air-trap may include a lower level sensor interface 506 and an upper level sensor interface 507. These two sensor interfaces communicate with a lower level sensor 245 and an upper level sensor 246, as shown and described in reference to FIG. 2d. When the level of fluid in the air-trap 110 drops below one or more of the sensors, for example, below both the upper level sensor interface 507 and the lower level sensor interface 506, a flow limiting mechanism, such as a tubing pinch clamp located at or about the fluid output port 505 closes. At approximately the same time that the flow limiting mechanism located at or about the fluid output port 505 closes, a flow limiting mechanism located at or about the air output port 504 opens. With the fluid output port 505 closed, fluid entering the air-trap 110 forces any air present in the air-trap, up the long axis of the air-trap. Because the air output port 504 is open, any air within the air-trap is forced out of the air-trap and into the air output tube 108 shown in FIG. 1. When the level of fluid in the air-trap 110 rises above the upper level sensor interface 507, the flow limiting mechanism at the air output port 504 closes. At approximately the same time that the flow limiting mechanism at the air output port 504 closes, the flow limiting mechanism at the fluid output port 505 opens again. With the fluid output port 505 open, fluid flow out to the patient via the primary outflow tube 111 is restored. The flow limiting mechanisms at or about each of the fluid output port and the air output port are further described as a fluid outflow flow limiting mechanism 240 and an air output flow limiting mechanism 241, respectively, in reference to FIG. 2d.

The air-trap embodied by the present invention is capable of functioning at varying inclinations and orientations. The cylinder formed by the air-trap is between 3 inches and 10 inches in height, preferably between 3.5 inches and 7 inches, and most preferably between 4 inches and 6 inches. The diameter of the air-trap cylinder is between 0.5 inches and 2 inches, preferably 0.625 inches and 1.5 inches, and most preferably 0.75 inches and 1.25 inches. The air-trap is able to properly remove air from the fluid as it passes through, even when the air-trap is tilted off its vertical axis between 10° and 90°, though most preferably up to 45°.

Heat Exchanger and Heating and Cooling Elements

Figure 7:
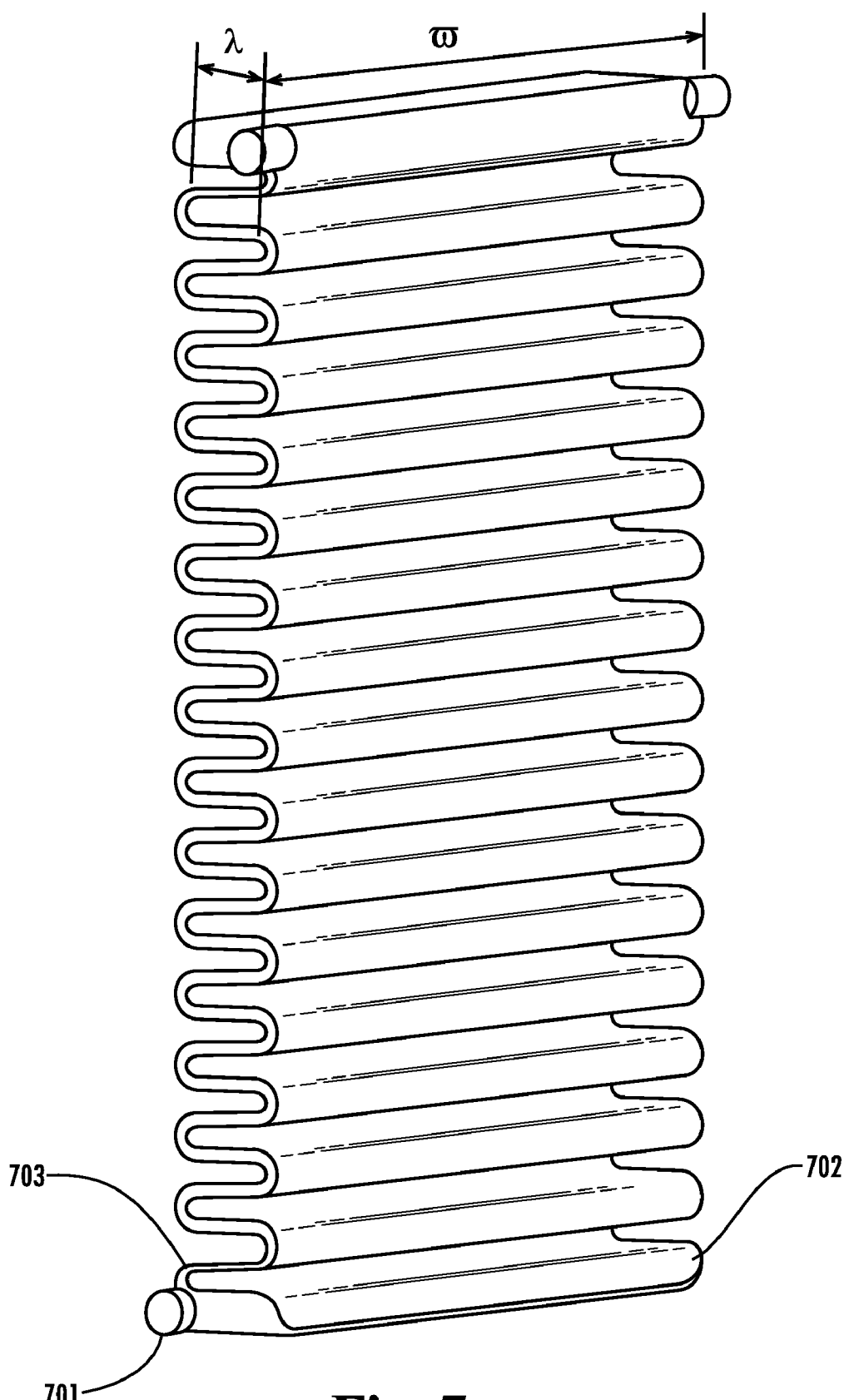
FIG. 7 shows the shape of fluid that would fill a heat exchanger in accordance with an example of the present invention.

As discussed above, efficient transfer of heat, to or from the infusion fluid, to be warmed or cooled impacts the present invention. Heating infusion fluid is first described, followed by illustrative examples of cooling infusion fluid. It is appreciated that where heating by the heating element is described, a cooling element may alternatively be used to cool infusion fluid in a similar manner. The present invention's use of a wide flow, short linear travel flow pattern allows for a more turbulent flow with an extremely large contact area. The contact area being described is the area of interface between the heat exchanger and the fluid passing through. Described as a ribbon of fluid, the fluid traveling through a heat exchanger, made in accordance with the present invention, will flow in very short linear distances along the short segments of linear distance, but will instead be proportionately wider. In fact, the flow cavity created for fluid flow through the heat exchanger is wider than it is long, and longer than it is deep, thereby creating a tortuous ribbon shape for the fluid to pass through. FIG. 7 is a representation of the fluid flowing through the heat exchanger 101. The fluid flow of FIG. 7 first is shown as having filled the exchanger inlet port as the inlet fluid 701. The fluid then fills the flow cavity as cavity fluid 702. The fluid then flows up the heat exchanger, first through the smaller gap created by the flow fin indicated as the first restricted flow 703. It should be noted that linear flow distance $\lambda$, defined by the height of the fins and representing the short segments of flow length, is less than the flow width $\omega$. The ratio between the linear flow distance $\lambda$ and the flow width $\omega$ can be from about 1:2 to 1:50, preferably from 1:4 to 1:25, and most preferably from 1:5 to 1:10. It is the ratio between the linear flow distance and the flow width which creates the ribbon-like flow pattern depicted in FIG. 7. By having such a short linear flow, the fluid flows through the heat exchanger with more turbulence than a typical long linear flow serpentine path. The introduction of turbulence in the fluid avoids the laminar type flow that such a serpentine flow path may create. As opposed to merely the molecules within the central portion of the fluid flow, that is those molecules not located directed at the interface, changing over faster than the molecules at the interface, the turbulent flow created by the present invention exposes more fluid molecules to the interface, which allows for an enhanced heat transfer. Likewise, this turbulent flow creates more contact between the molecules within the fluid flowing through the heat exchanger. With more contact between the molecules within the fluid, more heat exchange and transfer can occur, driving the efficient exchange of heat to or from the exchanger to the fluid to be delivered to the patient.

A heat exchanger made in accordance with the present invention creates this turbulent flow path and maintains it as the fluid flows over the fins. The fins 302, as depicted in FIG. 3, create one-half of the flow path for the fluid to follow. The fins on the same side of the heat exchanger are evenly sized and spaced, that is the distance between a first fin 307 and a second fin 308 is the same across the overall span of the heat exchanger. For the purposes of heat transfer involving a fluid flowing in the heat exchanger, the distance between a first and second fin of the same plurality of fins can be from 0.25 inches to 0.5 inches, preferably from 0.35 inches to 0.45 inches, and most preferably from 0.37 inches to 0.43 inches. The length of the fins on one-half of the heat exchanger dictates the linear flow distance. The length of the fins can be from about 0.25 inches to 1.0 inches, preferably from 0.5 inches to 0.8 inches, and most preferably from 0.6 inches to 0.7 inches. The flow path also contains a depth element created by the separation distance between the top of the fins in a first plurality of fins and the valley between two fins in a second plurality of fins. The flow path can have a depth of about 0.01 inches to 0.25 inches, preferably 0.03 inches to 0.125 inches, and most preferably 0.04 inches to 0.110 inches. The width of fins can be from 3 inches to 6 inches, preferably 3.5 inches to 5 inches, and most preferably 4 inches to 45 inches. Again, it is appreciated that in other embodiments, however, the heat exchanger 101 may provide a discrete flow path, such as a serpentine flow path, through which fluid may be directed.

For temperature control, transferring heat energy to or from the heat exchanger 101 occurs at an exposure surface 225 of the heat exchanger, the portion not covered or contained within the disposable cartridge, as shown in FIG. 2d, and from a thermal element contained within the pump housing. The thermal element may be a heating element 810 or a cooling element 850. The heating element 810 may be constructed as a power resistor-based heating element, an inductor-based heating element, a microwave-based heating element, radiant heating element, or the like, as is known in the art. The cooling element 850 may be a thermoelectric cooler, as is known in the art. Further, it is appreciated that a combination of one or more of the aforementioned thermal elements may allow for selectively adjusting between heating or cooling capabilities in a single device.

The exposure surface 225 of the heat exchanger, visible in FIG. 2d, is exposed from the housing of the disposable cartridge 100. The disposable cartridge 100 is removably attached to the pump device via one or more attachment points 210. The embodiment, as illustrated in FIG. 2d, includes a first attachment point 210 and a second attachment point 210. The attachment regions allow the disposable cartridge 100 to be affixed to the pump housing 250 securely and tightly. It is important that the exposure surface 225 of the heat exchanger 101 be located as uniformly close to the heating platen 275 as possible. Even known smooth materials, when dealing with solids, are rarely completely in contact when considered at a microscopic level. Therefore, the exposure surface 225 should be reasonably uniform and smooth in order to achieve as much surface area contacting the heating platen 275 as possible. The surface area of the exposure surface 225 which contacts the heating platen 275 can be from about 20 square inches to about 100 square inches, preferably from about 25 square inches to about 50 square inches, and most preferably from about 30 square inches to about 45 square inches. Likewise, the pressure exerted onto the disposable cartridge 100 to hold the exposure surface 225 in close contact with the heating platen 275 must increase if the surface of the exposure surface 225 and the heating platen 275 are not smooth. If the exposure surface 225 and the heating platen 275 are positioned immediately next to one another, it is considered that an air interface exists between the two surfaces. While the surfaces will be extremely close and pressure will be exerted on the exposure surface 225 such to press the two surfaces together, gaps between the surfaces may remain. It is therefore possible to reduce these gaps by coating the heating platen 275 with a thermal pad 840, which conforms and fills the voids between the surfaces with a material that is a better heat conductor than air, yet allowing a reasonable contact pressure to be used. If air serves as the interface between the surface of the exposure surface 225 of the heat exchanger and the heating platen 275, then greater pressure must be exerted on the system in order to achieve an efficient transfer of heat energy. Using a material that fills the gaps and is a better heat conductor than air allows the system to be established with a lesser and more reasonable pressure applied to the surface interface. Alternatively, the exposure surface 225 may be coated with the thermal pad 840 to similarly fill the voids caused by surface gaps. Furthermore, the compressive force exerted by engaging the engaging actuator and clamping mechanisms will further facilitate the coupling of the exposure surface 225 with the heating platen 275. It is appreciated that for some thermal elements, for example a heating element including a radiant heat source, a high pressure coupling of the exposure surface 225 with the heating platen 275 is not as important as for the embodiment including a power resistor-based heating element. Accordingly, less compressive force may be applied.

It is appreciated that while a substantially flat exposure surface 225 and a substantially flat heating platen 275 are described and illustrated in the figures herein, the exposure surface and the heating platen may be formed in other shapes. The exposure surface and the heating platen formed in other shapes, however, should still be formed so that the two are able to male, so as to be positioned immediately next to on another and minimize the gaps between the two. Reasons for configuring the exposure surface 225 and the heating platen 275 in other than a substantially flat configuration may be for manufacturing efficiency, or to increase the exposure surface area, as well as for other reasons as are appreciated by those skilled in the art.

Figure 2C:
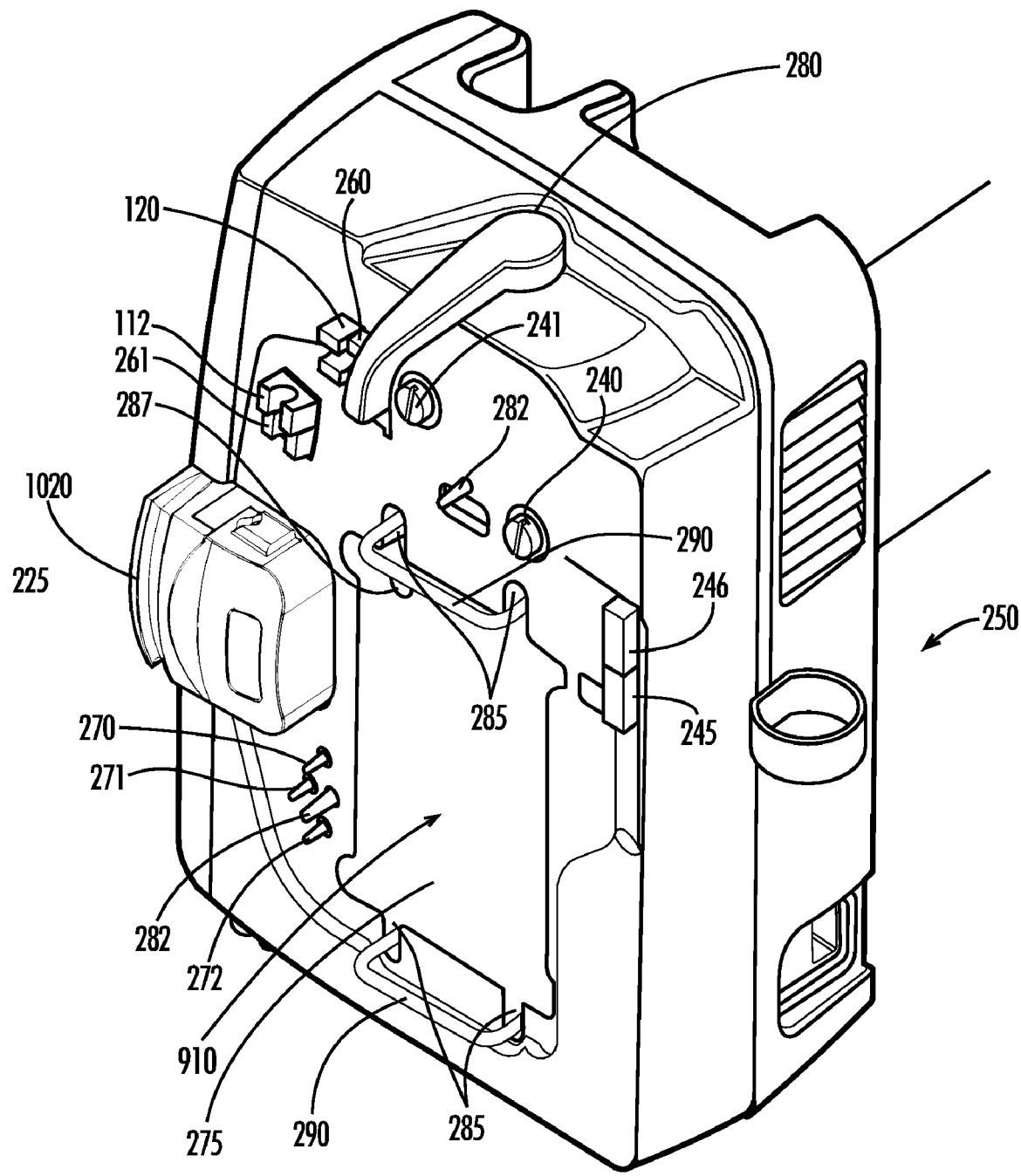
FIG. 2c shows the pump housing with exposed platen embodying an example of the present invention.
Figure 2D:
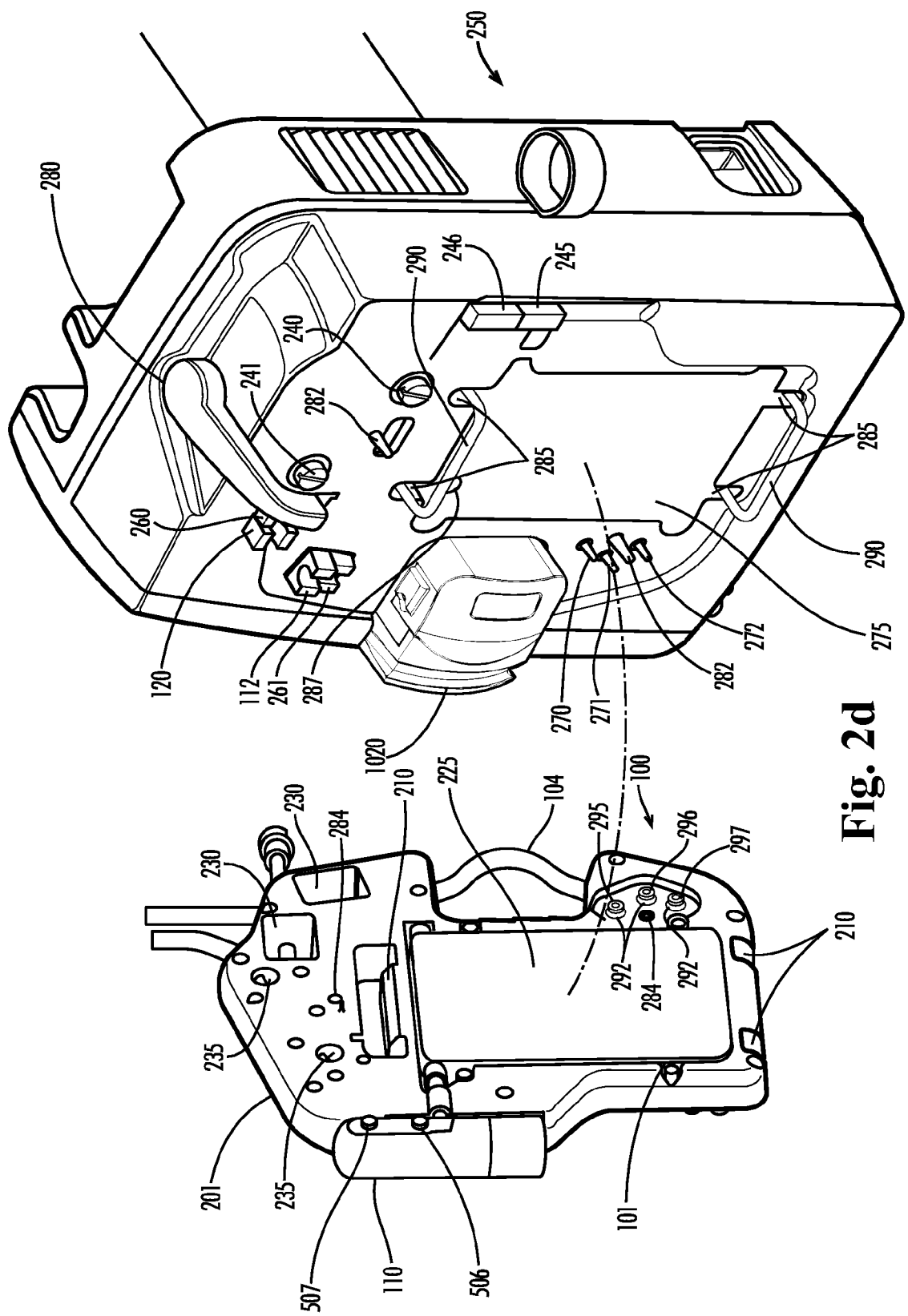
FIG. 2d shows the pump housing as it aligns with the disposable cartridge in accordance with an example of the present invention.

The disposable cartridge 100 may be removably attached to the pump housing 250 by an engaging actuator 280, as depicted in FIG. 2c. The engaging actuator 280 cooperates with one or more clamping mechanisms 290 extending from one or more lock housings 285 located around the heating element 810. In one embodiment, the engaging actuator 280 may be a handle, constructed as a lever, as is shown in FIG. 2c. However, in other embodiments, the engaging actuator 280 may be a knob, an electromechanical activated mechanism, or the like, as is known in the art. When the engaging actuator 280 is manipulated, the clamping mechanisms 290 extend from the pump housing 250 and may engage the disposable cartridge 100 at attachment points 210. In one embodiment, the clamping mechanisms 290 may be constructed like a bail and the attachment points 210 may be constructed like brackets having a lipped edge that extend away from the exposure surface 225. In this embodiment, the clamping mechanisms 290 may have an interior space that may engage the bracket shape of the attachment points 210 and secure the disposable cartridge 100 to the pump housing 250. Though, it is appreciated that other attaching means that may cause the disposable cartridge 100 to be releaseably secured to the pump housing 250 as are commonly known in the art. When engaged, the engaging actuator 280 may cause compressive force of approximately 100 pounds to 500 pounds, preferably about 200 pounds to 300 pounds, most preferably about 250 pounds, to be distributed across the surfaces of the heating platen 275 and the exposure surface 225. As described above, the compressive force created by the engaging actuator 280 facilitates mating of the two surfaces and improves heat transfer between the heating platen 275 and the exposure surface 225. Further, when the disposable cartridge 100 is fully engaged with the pump housing 250, by way of the clamping mechanisms 290, safety interlocks may be activated so as to signal that it is acceptable to begin operation. Some advantages that the clamping mechanisms 290 and the engaging actuator 280 have over the prior systems used for coupling two components, such as pneumatically engaged pistons or two-sided clam shells, are their ease of use, lighter weight and smaller sizes. As compared to previous pneumatic systems, the clamping mechanisms of the present invention generally require less force, and can be engaged by an operator using only a single hand. Additionally, after aligning the disposable cartridge with the pump housing, the disposable cartridge may be loosely secured to the pump housing, so as to allow the operator to let go of the disposable cartridge before finally engaging the engaging actuator. It is appreciated that in other embodiments, the engaging actuator need not create as much as 100 pounds of compressive force. For example, as stated previously, for an embodiment having a radiant heat source for the thermal element, high-pressure coupling is not as necessary. In an embodiment such as that, only enough compressive force as is required to properly align, mate, and engage the sensors with their respective interfaces and/or receptors is necessary.

Figure 8A:
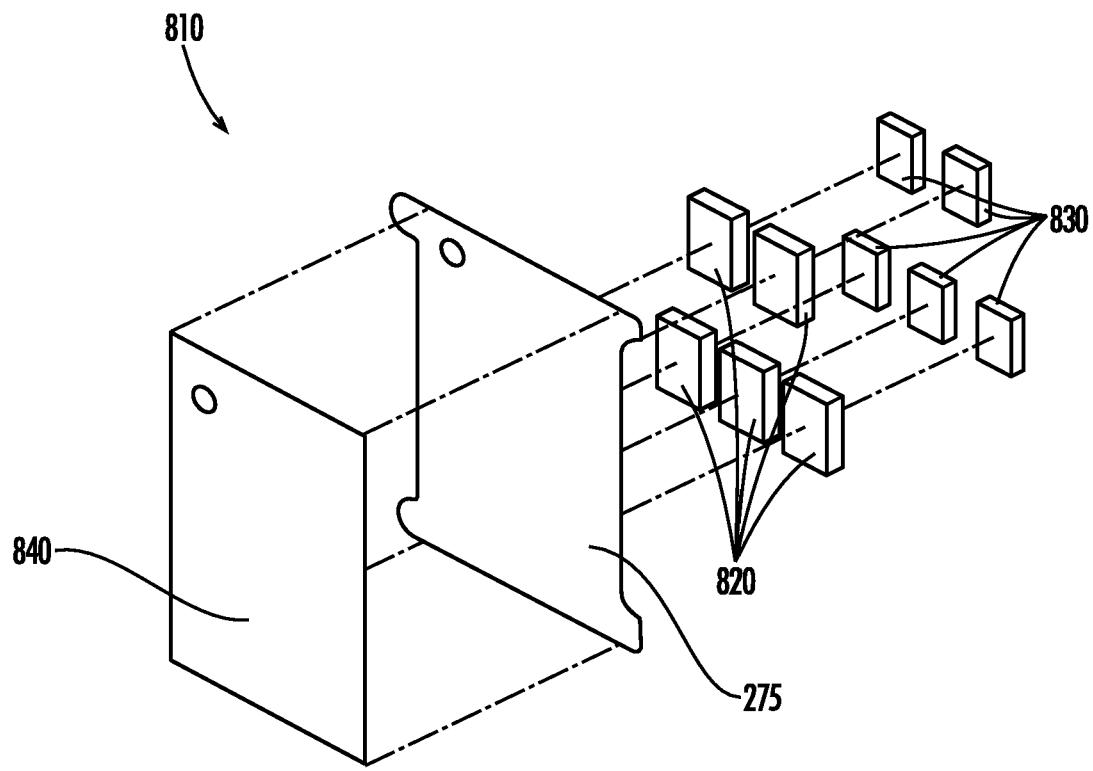
FIG. 8b shows an exploded view of an exemplary cooling element in accordance with an example of the present invention.

In one embodiment, the thermal element may be a heating element 810 as described in FIG. 5a. The heating element 810 generates heat energy from multiple power resistors 830 indirectly communicating with the heating platen 275. The power resistors 830 may directly communicate with one or more power insulators 820, which mate with the heating platen 275. The power insulator or insulators 820 may be constructed of aluminum oxide having a thermal conductivity of about 20 W/m-K or greater, and preferably about 30 W/m-K or greater, or other materials known in the art to have similar thermal conductance properties. The power insulators isolate the resistive load power from the heat exchanger 101 while still allowing efficient heat transfer and sinking properties to transfer heat to and from the heating element 810. Additionally, in one embodiment, thermal grease or thermal bonding compound, as is known in the art, having nominal thermal conductivity of about 5 W/m-K or greater, preferably between about 8 W/m-K and about 10 W/m-K, may be interposed between the heating platen 275 and the power insulators 820, and between the power insulators 820 and the power resistors 830. Alternatively, however, the power resistors 830 may be printed or deposited directly onto the power insulator 820, as is known in the art. The specific embodiment illustrated in FIG. 8a shows each power resistor 830 in communication with individual power insulators 820, which are in communication with the heating platen 275.

The resistors 830 are preferably connected, so as to limit the amount of capacitive coupling or capacitance leakage that occurs. Limiting capacitive coupling is beneficial because it reduces current leakage between the heating element 810 and the heat exchanger 101, and thus the infusion fluid, reducing the risk of causing electric shock to the patient. In a preferred embodiment, capacitance leakage for the pump device is less than 100 picofarads, and current leakage from the pump device to the patient is less than 10 microamperes, and from the pump device to a ground is less than 100 microamperes. Capacitive coupling may be reduced by creating multiple heat points, instead of a single heat point on the heating platen 275. In one exemplary embodiment, shown in FIG. 9, although any number of resistors 830 in any configuration may be employed, five power resistors 830 connected in parallel, each having a resistance of about 40 ohms to about 60 ohms, and preferably about 50 ohms, may be connected such that three power resistors 830 create three heat points on the lower portion of the heating platen 275 and two power resistors 830 create two heat points on the upper portion of the heating platen 275. In the preferred embodiment between three to five, most preferably five, power resistors may create heat points on the heating element. It is appreciated that other circuit designs may be employed that create about 10 ohms of total resistance and produce multiple heat points on the heating element, while still limiting capacitance leakage to about 100 picofarads, current leakage to the patient to about 10 microamperes, and current leakage to the ground to about 100 microamperes. The heating element 810 of this embodiment may be configured so as to heat the fluid between about 35° Celsius to about 50° Celsius. In some embodiments, the heating element 810 may heat the fluid from about 37° Celsius to about 43° Celsius.

The heating platen may be constructed from aluminum alloys because they are lightweight and have high thermal conductivity. It is appreciated that other materials, known in the art as having similar mass and conductivity properties, may also be used to construct the heating platen. For example, the heating element may also be constructed from copper, gold, silver, carbon, ceramics, or the like, as is known in the art. Further, it may be preferred to harden the aluminum alloy of the heating platen to prevent substantial yielding that may result from the compressive force exerted during clamping the disposable cartridge to the pump housing.

Figure 8B:
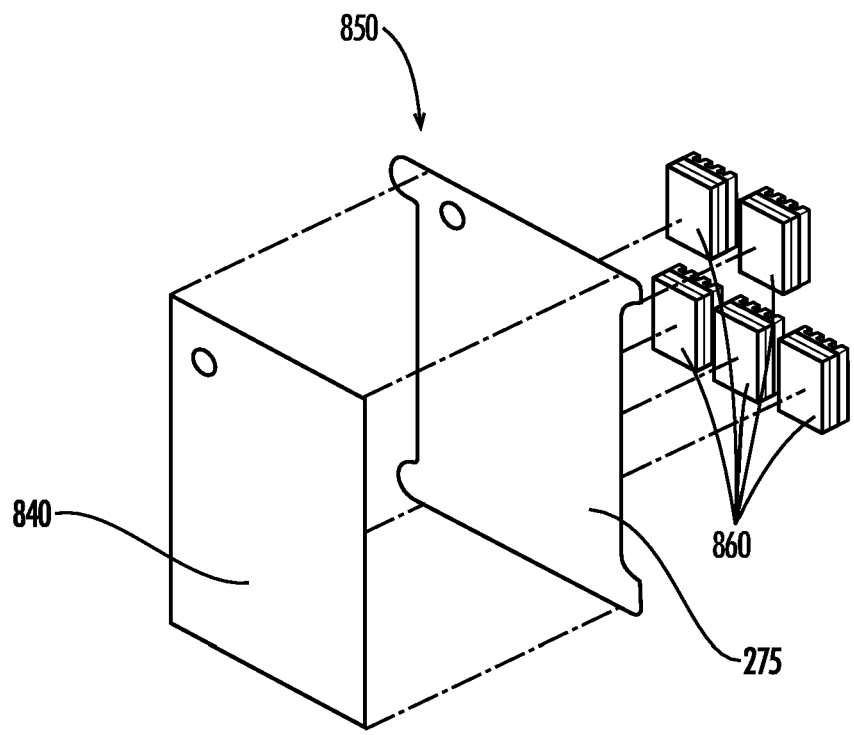
Figure 9:
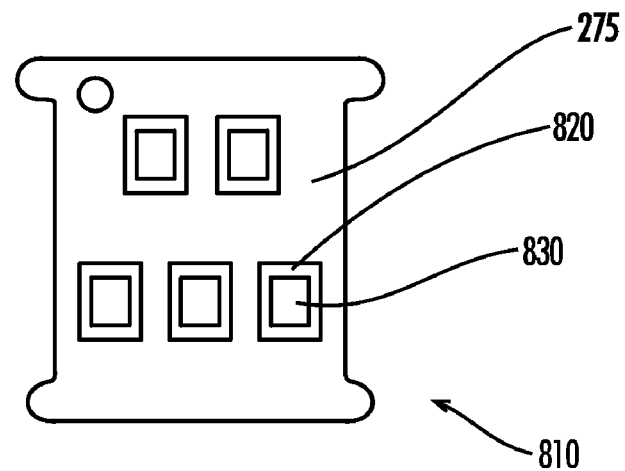
FIG. 9 shows a transparent view of an exemplary heating element, including a plurality of heat points in accordance with an example of the present invention.

In an alternative embodiment, such as that shown in FIG. 8b, the thermal element may be a cooling element 850, instead of the heating element, to cool fluid before delivery to a patient. The cooling element 850 may include the same heating platen 275 as is included in the heating element. It may further be constructed from one or more thermoelectric coolers 860, as are known in the art, mated against the heating platen 275. It is appreciated that in an embodiment including thermoelectric coolers 860, capacitance leakage and current leakage may be limited as described above in reference to FIG. 5a. Additionally, the cooling element 850 may have thermal grease or thermal bonding compound interposed between the heating element 275 and the thermoelectric coolers 860, like that described above in reference to the heating element 810. The thermoelectric coolers 860 may, by way of heat transfer from the heat exchanger through the thermoelectric coolers 860, create one or more cooled points on the heating platen 275. Cooling the heating platen 275 to a temperature below that of the heat exchanger 101 allows heat energy to transfer from the heat exchanger to the cooling element 850, and effectively lowers the temperature of the fluid circulating through the heat exchanger 101. The cooling element 850 may preferably be controlled using pulse-width modulation (PWM) to vary the power supply voltage to each of the thermoelectric coolers 860.

The thermoelectric cooler 860 may preferably be a peltier device or peltier thermoelectric cooler, as is known in the art. A peltier thermoelectric cooler 860, as may be used in the present invention, preferably includes an array of n-type and p-type semiconductors interposed between two ceramic insulators. The n-type and p-type semiconductors may be n-doped bismuth telluride and p-doped bismuth telluride pellets, respectively, or the like, as is known in the art. The thermoelectric cooler may also include a heat sink on the side opposite that interfacing with the heating platen 275, so as to efficiently remove heat from the heating platen and the cooling side of the thermoelectric cooler 860. The cooling element 850 in this embodiment may be used to cool infusion fluid to temperatures in the ranges between about 0° Celsius to about 37° Celsius, more specifically to about 4° Celsius to about 25° Celsius.

It is further appreciated that an embodiment that includes a thermoelectric cooler 860 configured as a peltier device, as described herein, may be used as a thermoelectric heat pump, so as to create a heating and cooling element. An embodiment configured in this manner, so as to include a heating and cooling element, allows for selectively heating or cooling the heat exchanger on the heat pump. As is known in the art, a peltier device can be configured to source heat, when current flows in one direction, and sink heat when current is reversed in the opposite direction. Accordingly, a pump device configured in this manner may allow for using a single device to selectively heat or cool fluid as desired by the user.

In another embodiment including a thermoelectric cooler 860, the thermoelectric cooler may act as a thermoelectric heat pump, as is known in the art, providing a heating and cooling element for the pump device. More specifically, a thermoelectric heat pump that is a pettier device may source or sink heat, depending upon the direction of the current flow through the thermoelectric cooler. Accordingly, in an embodiment including a thermoelectric cooler/heat pump 860, the central controller may be configured to allow the user to selectively control the current flow through the heat pump, thus allowing the thermal element to create both heat points and cooling points on the heating platen 275.

Dynamic Range Motor and Pump

The pump device includes a pumping mechanism that is driven by a dynamic range motor drive assembly to pump the fluid from the fluid supply, through the heat exchanger, then to the patient. It is appreciated that other aspects, described in the present application, may provide additional functionality and paths through which the fluid may flow between the supply and the patient. The pumping mechanism may be a roller head occlusive pump. The rotating action of the pump roller head assembly imparts a directional, peristaltic motion to fluid existing in the pump loop that is contained within the pump chamber. In other embodiments, the pumping mechanism may be another type of peristaltic pump, for example, a non-circular peristaltic pump, a centrifugal pump, an impeller, or the like, as is known in the art for pumping fluids through malleable tubing. The motor drive assembly may be electronically controlled, for example, by a digital signal processing controller (DSP controller), as further described herein. In one embodiment, the pumping mechanism and motor drive assembly, in combination, are capable of delivering about 1 milliliter of fluid per hour to at least about 3000 milliliters of fluid per minute. Though, in some embodiments, the pump device may only be required to pump between 10 milliliters of fluid per hour to about 1200 milliliters of fluid per minute (e.g., during typical blood replenishment or replacement procedures), while in other embodiments the preferred range may be between 2000 milliliters and 8000 milliliters of fluid per minute (e.g., for delivery during emergency heart and lung procedures). In another embodiment, the pumping mechanism and the motor drive assembly are capable of maintaining delivery of fluid at predetermined pressure ranging from about 0 mmHg to about 750 mmHg.

Figure 10:
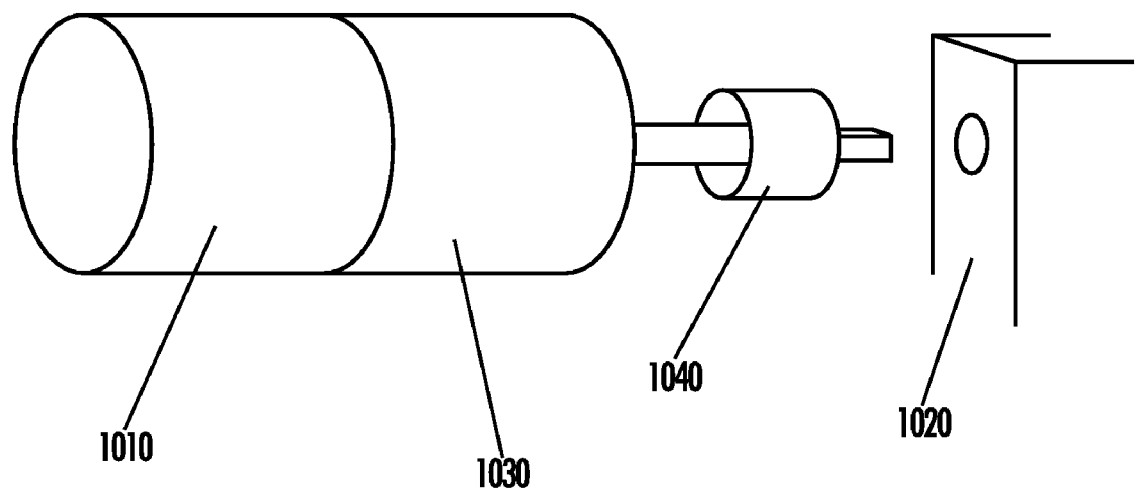
FIG. 10 shows a motor drive assembly and pumping mechanism that would be integrated within the pump housing in accordance with an example of the present invention.

A motor drive assembly may be used to drive the pumping mechanism shown in FIG. 10. The motor drive assembly may include a motor 1010, which may be a DC motor, preferably a brushed DC motor, as is known in the art. One example of a brushed DC motor that may be used is Maxon Motors REmax motor (part no. 118751), rated at 20 Watts at a nominal voltage of 18 Volts DC and having a no-load speed capability of 10,200 revolutions per minute. The motor drive assembly may also include a gear assembly 1030. The motor 1010 may communicate with the gear assembly 1030 so as to scale the rotation speed of the motor to ranges acceptable by the pumping mechanism. The gear assembly, however, operates in a static configuration, wherein the gear ratio is fixed and does not change during operation. In a preferred embodiment, the gear assembly 1030 may provide an approximate 14:1 gear ratio. It is appreciated that other gear ratios may be used, depending upon the rotation speed of the motor used, the configuration of the electronic motor controller, and the pumping mechanism requirements. One example of a gear assembly for use in the present application is Maxon Motors Planetary Gearhead GP 26 B (part no. 144029). The motor 1010 and gear assembly 1030 are integrated within the pump housing 250. The motor 1010 is preferably connected to and controlled by an electronic controller. Additionally, the motor 1010 is connected to a power source to supply voltage across its terminals, as described below. It is appreciated that the combination of the motor drive assembly and the electronic controller allows for dynamically selecting wide flow ranges, for example, from 1 milliliters per hour to 8000 milliliters per minute, with the use of a single motor and without the further use of additional stepper motors or differential drives.

The motor 1010 and gear assembly 1030 communicate with the receiver of the pumping mechanism 1020. A coupler 1040 may be used to couple the output shaft of the gear assembly 1030 to the receiver of the pumping mechanism 1020. In one embodiment, the pumping mechanism 1020 may include a pumphead with multiple rollers, preferably three, that successively engage then release the tubing of the pump loop 104 within the pump chamber. Turning the roller heads and rollers causes occlusive pumping, as is known in the art.

The pump loop 104 preferably consists of at least one section of collapsible tubing, through which the fluid will flow upon initiation of pumping action. The pump loop tubing may have a thinner wall than other infusion tubing, allowing for easier pumping action by the roller pumphead. However, harmonics resulting from the pumping motion imparted on the pump loop tubing may cause fill and rebound cycles in the tube behavior, and thus may cause variability in flow rates or flow pressures. Thus, it may be preferable to reduce the fill and rebound behavior by controlling the length of the tubing in the pump loop 104, and thus the tension of the pump loop 104, when engaged with the pumping mechanism. Controlling the tension of the pump loop 104 effectively creates a tube having a shorter, fixed length, thus producing flow behavior more predictable than a tube having a greater length or a variable length. This may be accomplished by securing the tubing of the pump loop 104 at fixed points on the disposable cartridge, at a point or points before the portion of the tubing that engages the pump head, and at a point or points after the portion of the tubing that engages the pump head. In one embodiment, as illustrated in FIG. 1, the pump loop 104 may be constructed from a different tubing having a different wall thickness than the primary inflow tube 102 and the pump outflow tube 109. The pump loop 104 may be coupled, by methods known in the art, to the primary inflow tube 102 and the pump outflow tube 109. Thus, the ends of the pump loop 104 may be affixed to the disposable cartridge, so as to control its tension and tube length, where the pump loop 104 couples with the primary inflow tube 102 and the pump outflow tube 109. In this embodiment, a tubing coupler 113 connecting the tubes may be permanently affixed to the disposable cartridge, and the tubing ends slide thereover. Further, the tubing may be secured over the tubing coupler 113 by methods known in the art, such as a self-tensioning clip surrounding the tube ends over the tubing coupler 113. It is appreciated that other means of securing the ends of the pump loop 104 to the disposable cartridge, as are known in the art, may be employed. Accordingly, in this embodiment the tube tension and length through the pumphead may be advantageously controlled by affixing each end to the disposable cartridge, so as to reduce variability in pressure and flow rates.

The Watson-Marlow 313D pumphead (part no. 033.3401.000) is an example of a three-roller pumping mechanism, configured for use with tubing having 1.6 millimeter walls, and for providing 3 milliliter per revolution flow rate. The Cole-Parmer peroxide-cured silicon tubing (part no. K-06411-71) is an example of tubing for use in the pump loop, having an inner diameter of 6.4 millimeters and a wall thickness of 1.6 millimeters, that may be used with the pumping mechanism. It is appreciated that other pumping assemblies and tubing configurations, as are known in the art, may be used in embodiments of the present invention, such as two or four roller pumpheads or pumpheads, non-circular peristaltic pumps, centrifugal pumps, impellers, or the like, as is known in the art. Additionally, the infusion tubing in the pump loop may be configured to have different tube bores and wall thicknesses. Alternative combinations of pumping mechanisms and tubing sizes will yield different flow rate ranges, as is known in the art.

Figure 11:
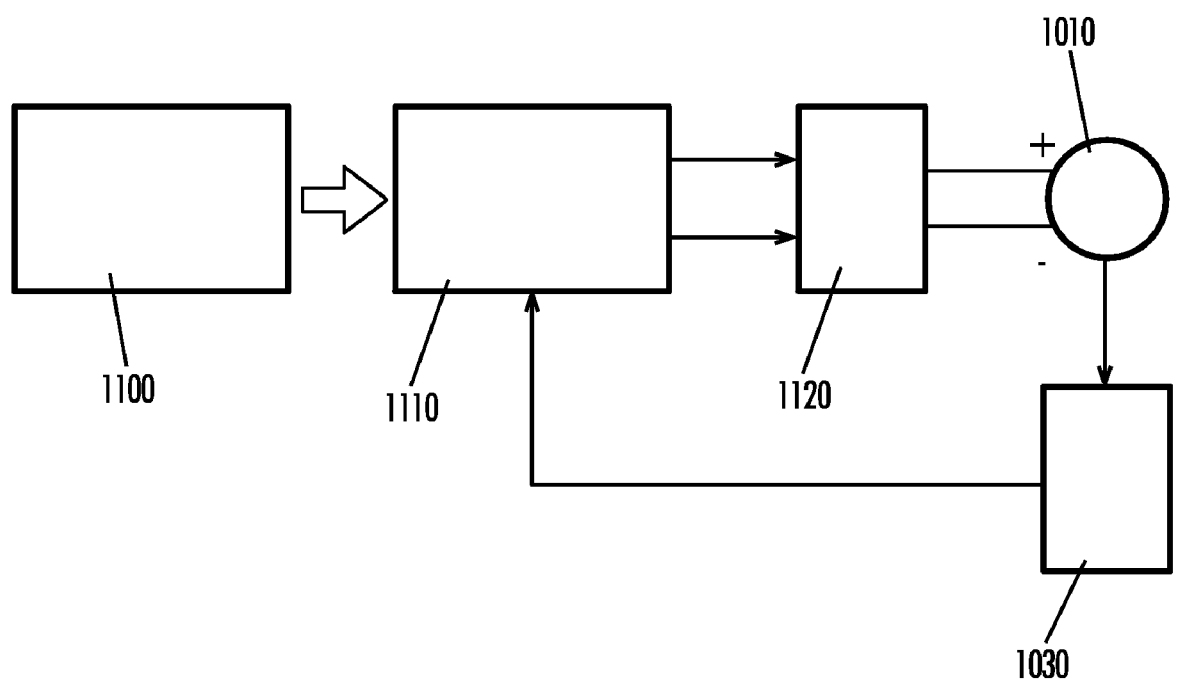
FIG. 11 shows an exemplary functional block diagram of the electronic motor controller in accordance with an example of the present invention.

The motor 1010 may be controlled by an electronic controller 1110 as is described by the functional block diagram in FIG. 11. The electronic controller 1110 may be a DSP controller that receives a signal from the user input control and converts it into a pulse-width modulation (PWM) signal that ultimately dictates the speed of the motor. A PWM signal controls the speed of the motor by signaling a maximum voltage, 10 volts, for example, to be applied across the motor and a minimum voltage intermittently. The duration at which the voltage is fully on, referred to as the "duty cycle," may be varied, which in turn varies the speed of the motor. A duty cycle of 100%, for example, would turn the motor at its maximum speed, because the voltage across the motor would always be fully on; whereas a duty cycle of 75% will reduce the speed of the motor, because the time during which the max voltage is applied is decreased. Preferably, the electronic controller 1110 is a high resolution DSP controller, preferably about a 16-bit to about a 64-bit processing controller, and more preferably about a 32-bit processing controller. The electronic controller 1110 may be integrated with motor power drive circuitry 1120 to control the current flowing through the motor 1010, as is known in the art. A tachometer 1130, or an encoder, may be integrated within the system to sense the number of revolutions at the motor and provide feedback to the electronic controller 1110 and the device central controller 1100. The tachometer allows the electronic controller 1110 and the central controller to know the flow rate of the device, by sending information directly related to the number of revolutions over time, which is then used to calculate flow rates, because the flow rate per revolution is known based on the infusion tubing and pumphead configuration. The higher the tachometer's resolution—the number of counts per revolution of the motor shaft—the more accurate the DSP controller will be during operation. In a preferred embodiment, the tachometer has between about 250 lines of resolution to about 1000 lines of resolution, and more preferably, has about 500 lines of resolution. An example of an electronic DSP controller for use in an embodiment of the present invention, is National Semiconductor Precision Motor Controller (part no. LM629M-8). The LM629M-8 is a 24-pin surface mount controller that has 32-bit registers for velocity, position, and acceleration, and a programmable Proportional Integral Derivative (PID) filter with 16-bit coefficients to compensate for error, as detected in the feedback loop, as is known in the art. The LM629M-8 can interface with the National Semiconductor 3A, 55V, H-Bridge (part no. LMD18200), as power drive circuitry 1120, to receive the PWM and direction signals from the LM629M-8 and drive the motor 1010, as is known in the art. It is appreciated that the motor may be controlled by other means, such as a general-purpose computer having a communication link to send and receive signals, a memory, and programming logic or an analog controller, using resistive rheostat, or the like, as is known in the art.

The dynamic range motor drive assembly and disposable cartridge combination may provide flow rates of about 1 milliliter per hour to, at least, about 4000 milliliters per minute to satisfy the infusion needs from the low flow needs of Keep Vein Open (KVO) state to the rapid, high flow infusion of crystalloid, colloid, or blood product, including packed red blood cells. Further, in other fluid delivery uses, as described herein, the dynamic range motor drive assembly may provide flow rates between about 2000 milliliters per minute and 8000 milliliters per minute. It is appreciated that the user input may be configured so as to allow adjusting the flow rate in slight increments, as well as to allow for rapid adjustment of the flow rate. It is preferable, however, that a single selection (e.g., pressing the rate button once) will increase (or decrease) the flow rate by anywhere from approximately 5 milliliters to approximately 20 milliliters, and most preferably will increase (or decrease) the flow rate by approximately 10 milliliters. The ability to provide and control this broad range of flow rates may also be advantageously employed for infusion normothermic fluids into patients after surgery, or for treating or preventing hypothermia. Examples of fluids that may be delivered by the device are blood, crystalloid, colloid, saline, medication, any combination thereof, or the like, as is known in the art. Yet another beneficial use of a broad spectrum of flow rates is the high speed delivery of irrigation fluids which may be warmed.

The dynamic range motor drive assembly may be further configured to deliver fluid at a substantially constant infusion pressure, which may be predetermined by the user between about 0 mmHg and about 750 mmHg, and preferably between about 25 mmHg and about 150 mmHg. More specifically, the user input may be configured to allow the user to select the preferred pressure around which the delivery should be maintained. For example, the user may select to infuse fluid at a constant pressure of 45 mmHg, causing the central controller to signal to the dynamic range motor drive assembly to increase the fluid flow rate until 45 mmHg of pressure is achieved. After achieving the predetermined 45 mmHg of pressure (in this example), the motor and pump mechanism may slow, so as to reduce the fluid flow, in an effort to substantially maintain the predetermined pressure. When, however, the one or more pressure sensors sense that the pressure is falling below the predetermined pressure, the central controller will cause the motor and pump mechanism to increase the flow rate, so as to increase the pressure, until it reaches the predetermined pressure again. Accordingly, by making adjustments to the flow rate, the pump device is able to maintain a substantially constant pressure. It is appreciated that the adjustments to the flow rates may be minor adjustments, for example, 5-25 milliliters per minute, or may be more drastic adjustments, such as stopping flow altogether (i.e., 0 milliliters per minute). Pressure sensors contained in the disposable cartridge, such as the outflow pressure sensor, provide feedback to the control unit for proper adjustment of the DSP controller to maintain a constant pressure.

Attachment and Alignment

The components of the disposable cartridge that interface with the pump housing are advantageously arranged and designed, so as to allow simple, one-step attachment of the exchanger. FIG. 2d illustrates the alignment of the corresponding elements between the disposable cartridge 100 and the pump housing 250.

As described above, the exposure surface 225 of the heat exchanger 101 preferably mate with the heating platen 275 on the pump housing 250, so as to promote heat transfer by creating minimal air gaps between the two elements. Additionally each sensor located on the pump housing aligns and communicates with its corresponding mate on the disposable. There may also be an alignment mechanism, such as one or more guide pins 282 on the pump housing and corresponding guide receptors 284 on the disposable cartridge, to facilitate proper alignment when attaching the disposable cartridge to the pump housing. Proper mating also allows the heat exchanger temperature sensor 287 to communicate with, and accurately measure, the heat exchanger 101 temperature.

The disposable cartridge 100 may include one or more detector interfaces 230, allowing one or more sensors on the pump housing to correspondingly communicate with the infusion tubing on the cartridge. For example, a first detector interface 230 may allow the inflow bubble detector 120 and the inflow temperature sensor 260 to communicate with the infusion tubing 102, and the second detector interface 230 may allow the outflow bubble detector 112 and the outflow temperature sensor 261 to communicate with the outflow tubing 111 upon attaching the disposable cartridge to the pump housing. In one embodiment, as illustrated in FIG. 2d, the detector interfaces 230 may be formed as apertures and sensors on the pump housing, for example, the bubble detectors 120, 112, and the temperature sensors 260, 261, may extend therethrough to communicate with the infusion tubing contained inside the cartridge. Alternatively, in another embodiment, the side of the disposable cartridge interfacing with the pump housing may not include an exterior casing, leaving the infusion tubing exposed. In this embodiment, the detector interfaces 230 are simply the portions of the exposed infusion tubing that communicate with the sensors on the pump housing. The inflow and outflow bubble detectors 120, 112 may be ultrasonic sensors that are positioned within an open-ended, c-shaped, clamp-like receptacle that receives the infusion tubing and positions the ultrasonic sensors in close proximity to the tubing when in place. In other embodiments, the bubble detectors 120, 112 may be optical-based sensors, such as laser sensors using Doppler based calculations, or the like, as is known in the art. Similarly, the inflow and outflow temperature sensors 260, 261, which may be infrared sensors, are positioned within a similar open-ended, c-shaped, clamp-like receptacle, so as to be in close proximity to the tubing when in place. In other embodiments, the temperature sensors 260, 261 may be optical-based sensors, such as laser sensors, mechanical thermistors, or the like, as is known in the art.

Additionally, the primary inflow tube 102 and the primary outflow tube 111 may be lubricated, formed from a lubricious material, or the receptacles on the pump housing may be lubricated, so as to facilitate the mating between the infusion tubing and the inflow and outflow bubble detectors 120, 112 and the inflow and outflow temperature sensors 260, 261. Alternatively, the inflow and outflow temperature sensors 260, 261 and the inflow and outflow bubble detectors 120, 112 may be lubricated on their interior surfaces that engage and mate with the infusion tubing. The lubricant may be a heat resistant compound, such as silicone, or the like, as is known in the art. Furthermore, an energy transmitting material may be applied to either the infusion tubing and/or the bubble detectors 120, 112 and the temperature sensors 260, 261 to facilitate the transmission of energy from the sensor to the infusion tubing and fluid contained therein. For example, for ultrasonic-based sensors, a silicone based material may be used to facilitate transmission of sound energy. Alternatively, when including laser-based sensors, a non-refractive material may be used to facilitate the transmission of light energy.

The disposable cartridge may include one or more flow limiting interfaces 235 that align with one or more flow limiting mechanisms, which are used to restrict the flow of air or fluid through the infusion tubing at the position of the one or more flow limiting interfaces. For example, two flow limiting interfaces 235 may be formed as apertures on the disposable cartridge 100 and may allow for the fluid outflow flow limiting mechanism 240 and the air output flow limiting mechanism 241 to extend therethrough and engage the outflow tubing 111 and the air output tubing 108, shown in FIG. 1, so as to allow for preventing the flow through the respective tubing when engaged. The tubing flow limiting mechanisms 240, 241 may be solenoid activated clamps that, when activated, are retracted substantially within the pump housing, and, when deactivated, extend outwardly, engage the infusion tubing, and compress the tube to effectively prevent the flow. Flat surfaces may be aligned behind the infusion tubing within the disposable cartridge 100 to receive the infusion tubing as it is compressed by the tubing flow limiting mechanisms. Alternatively, in another embodiment, the side of the disposable cartridge interfacing with the pump housing may not include an exterior casing, leaving the infusion tubing exposed. In this embodiment, the flow limiting interfaces 235 are simply the portions of the exposed infusion tubing that communicate with the fluid outflow and air output flow limiting mechanisms 240, 241.

There may be one or more pressure sensors on the pump housing that communicate with pressure receptors on the disposable cartridge. In one embodiment, an inflow pressure sensor 270, a pump outflow pressure sensor 271, and a fluid outflow pressure sensor 272 extend through an inflow receptor 295, a pump outflow receptor 296, and a fluid outflow receptor 297, respectively. The pressure sensors may be, in one embodiment, sensor needles, and the pressure receptors may be orifices that receive the sensor needles. Upon attachment, the pressure sensors 270, 271, 272, by way of the pressure receptors 295, 296, 297, are in communication with the inflow, pump outflow, and fluid outflow pressure junctions 103, 105, 135 of the disposable cartridge. By extending into the pressure receptors 295, 296, 297, the pressure sensors 270, 271, 272 may open a check valve therein and communicate with a captured volume of gas (e.g., the first air chamber 151) between the pressure sensor and the fluid flowing through the infusion tubing, whereby the pressure of the captured volume of gas is directly related to the fluid pressure in the associated infusion tubing. This pressure may be sensed by pressure transducers in the pump housing in communication with each of the pressure sensors. In the embodiment, the pressure receptors may extend from the disposable cartridge and have an orifice, approximately the same, or preferably a slightly smaller, diameter as the outer diameter of the pressure sensors, through which the pressure sensors extend. The pressure receptors may be constructed from a polymer material that is pliable, so as to provide a tight seal around the pressure sensors, such as silicone, a silicone compound, or the like, as is known in the art. Further, in this embodiment, each pressure receptor may include a collar 292 extending from the disposable cartridge and surround the outside diameter of each of the pressure receptors. The collars 292 may be constructed from a hard material, such as a plastic, a metal, a composite, or the like, and may preferably be constructed from the same material as the cartridge from where the collars 292 extend. The collars 292 are included to prevent deformation of the pressure receptors, and to prevent the pressure receptors from separating from the pressure sensors when under high pressures, thereby allowing for continued accurate pressure monitoring. It is appreciated that, in other embodiments, the pressure sensors may not have a needle configuration, thus there may be no need for the receptors to have an orifice. Accordingly, the pressure sensors, described herein, are exemplary, and any other pressure sensors, as are known in the art, may be used.

There may be one or more sensors on the pump housing 250 that may align with one or more points on the air-trap. These sensors may detect the fluid level at the one or more points on the air-trap. The sensors may be ultrasonic sensors, optical sensor, such as a laser, or the like, as is known in the art for detecting differences in material properties. In one embodiment, the air-trap includes the lower level sensor interface 506 and the upper level sensor interface 507, as described above, in reference to FIG. 5, and the pump housing 250 includes a lower level ultrasonic sensor 245 and an upper level ultrasonic sensor 246. The lower and upper ultrasonic sensor interfaces 506, 507 utilize pads constructed from a material favorable to transmitting energy, such as silicone, urethane, or the like, as is known in the art, to mate with the lower and upper level ultrasonic sensors 245, 246. The pads of the ultrasonic sensor interfaces 506, 507 provide a material that improves the signal responses of the ultrasonic sensors, in order to effectively measure the level of fluid within the air-trap.

It is appreciated that the pump device and/or cartridge may contain other sensing devices than those previously described. For example, one or more blood sensors may be included on the pump housing to interface with one or more points on the infusion tubing, so as to monitor properties of blood flowing therethrough. The blood sensor may be an optical-based sensor, such as a raman laser, or the like, as is known in the art. The blood sensor may monitor blood properties or blood chemistry such as, but not limited to: blood hematology, electrolytes, enzymes, blood gasses, clotting indices, and glucose levels. Other blood chemistry characteristics may likewise be monitored or sensed, as is known in the art. Another example of an additional sensor that may be included in the pump device is a flow sensor. The flow sensor may be an ultrasonic sensor, an optical-based sensor, such as a laser sensor, a thermal sensor, or the like, as is known in the art.

Accordingly, each of the components described above properly align and engage with the pump housing upon attachment. To align the disposable cartridge 100 to the pump housing 250, the clamping mechanisms 290 of the pump housing shall be aligned with the attachment points 210 on the disposable. By aligning the clamping mechanisms 290 with the attachment points 210, the individual components are directly aligned with their complimentary mate. Alignment mechanisms, such as the one or more guide pins 282 on the pump housing and the corresponding guide receptors 284 on the disposable cartridge, may also be included to facilitate proper alignment when attaching the disposable cartridge to the pump housing. The guide receptors 284 may be configured as apertures having a diameter corresponding to that of the one or more guide pins 282. Closing the engaging actuator 280 will cause the clamping mechanisms 290 to pull the attachment points 210, and therefore the disposable, to mate with the pump housing and to interconnect each component pair. Furthermore, the pump housing 250 may include an install detector that determines whether the disposable cartridge 100 is properly aligned and attached. The install detector may be one or more switches that are tripped upon successfully attaching the disposable to the pump housing. The pump device may be configured to generate an alert or an alarm if the user attempts to begin operation without the install detector being tripped, or it may alternatively be configured to not power on or begin pumping unless the install detector has been properly tripped.

User Input and Control

Figure 12:
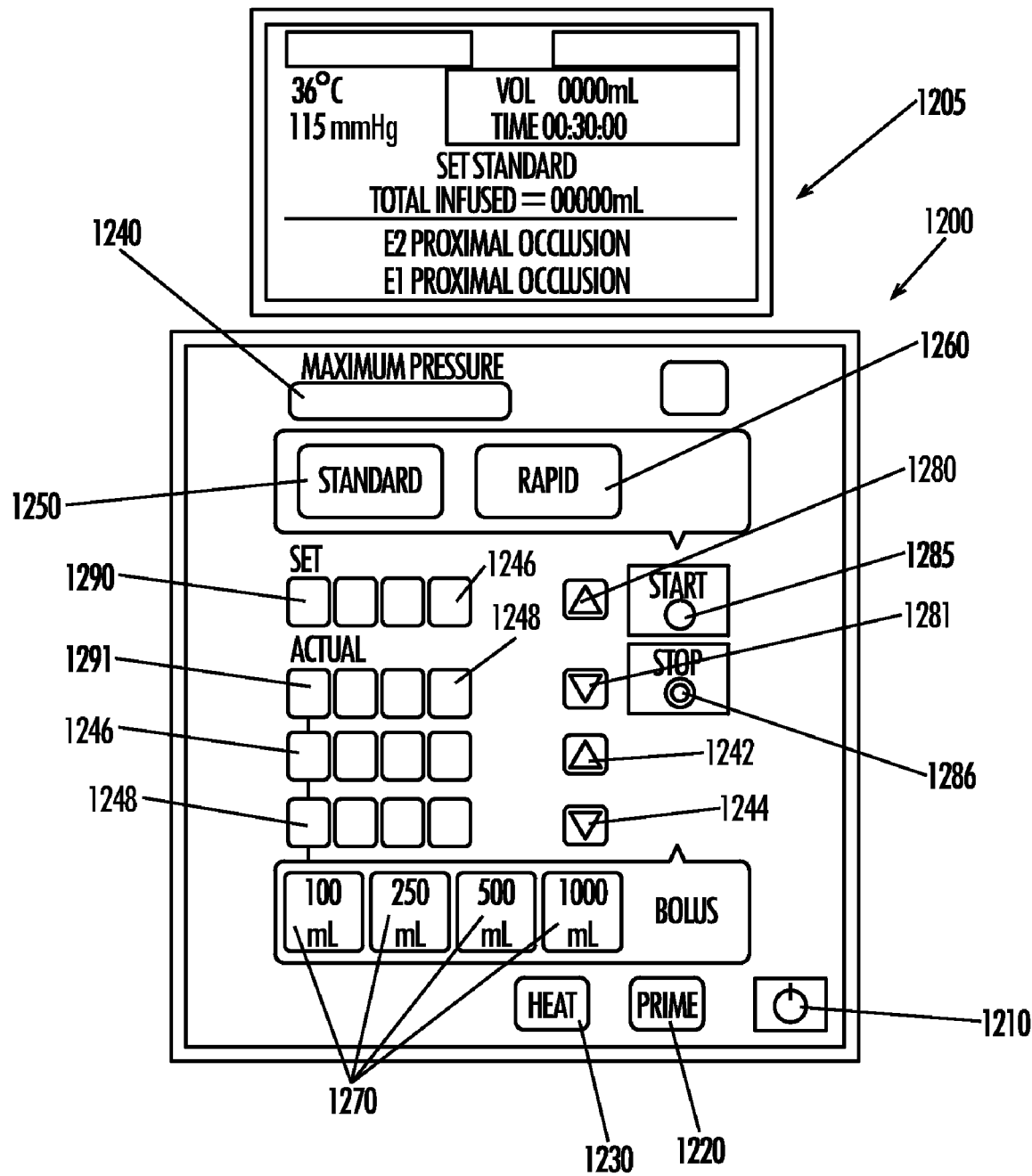
FIG. 12 shows an exemplary user interface panel and the status display panel in accordance with an example of the present invention.

The pump device allows user control through a simple user interface that offers easy access to primary functions by requiring minimal input selections by a user. FIG. 12 shows an example of an user interface panel 1200 of the present invention. The user interface panel 1200 preferably allows for only a single selection to cause the infusion device to perform time sensitive functions during operation. In an effort to promote efficient operation and fast response operation, multi-level menus are minimized, if at all, to those functions that are not time sensitive. Additionally, the device may be configured so as to allow the user to alter the operating states of the pump during operation, without having to halt the device and/or navigate through multi-level configuration or options menus.

Certain aspects of the present application reference block diagrams of systems, methods, and apparatuses, according to at least one embodiment described herein. It will be understood that each block of the block diagrams, and combinations of blocks in the block diagrams, respectively, can be implemented, at least partially, by computer program instructions, generally referenced herein as the central controller 1100. These computer program instructions may be loaded onto a general purpose computer, special purpose computer, special purpose hardware-based computer, or other programmable data processing apparatus to produce a machine, such that the instructions, which execute on the computer or other programmable data processing apparatus, create means for implementing the functionality of each block of the block diagrams, or combinations of blocks in the block diagrams, discussed in detail in the descriptions below.

The user interface control panel 1200 may include power input 1210 that turns the infusion device on, if it is not already on. If the device is already on, selecting the power input 1210 may cause the machine to go into standby mode if it is plugged in, or may turn off the infusion device if it is running on batteries or any other alternative power means. A prime input 1220 allows the user to select either manual prime, by continuously depressing the prime input 1220 for the duration for which priming is desired, or automatic prime, by selecting and releasing the prime input 1220. More details regarding the prime sequences are discussed below in reference to FIGS. 13-15. A heat input 1230 will allow the user to turn the heating element 810 on and off. In another embodiment, the user interface may include a cooling input in place of, or in addition to the heat input 1230 that allows the user to turn the cooling element 850 on and off, if included in the device.

One or more maximum pressure inputs 1240 may allow the user to select the maximum pressure tolerated in the infusion tubing. For example, the pump device may include two maximum pressure inputs 1240, such as 100 mmHg and 300 mmHg, and if one or more of the pressure sensors sense a pressure exceeding the pressure level corresponding to the maximum pressure input 1240 selected, the device may reduce the flow rate, or stop pumping fluid and alert the user of the excessive pressure in the system. For example, during operation, if a flow rate of 500 milliliters per minute and a maximum of 100 mmHg is selected, the device will increase the flow rate until 500 milliliters per minute is achieved, unless the pressure reaches or exceeds 100 mmHg. If the pressure reaches or exceeds the selected limit, the device will slow the flow rate so as to allow the pressure to drop. After the pressure drops, the device will increase the flow rate again until the flow rate is reached, repeating the cycle until the selected flow rate is achieved without exceeding the pressure maximum. Similarly, the pump device may include a pressure increase input 1242 and a pressure decrease input 1244, by which the user may pre-define a pressure to be maintained by the pump device. The pump device may further include one or more preset pressure inputs, which will allow the device to maintain the flow pressure corresponding to the pressure preset selected. The pressure maintenance level may be displayed in a selected pressure indicator 1246. An actual pressure indicator 1248 may display the actual pressure during operation. Using the pressure increase input 1242 and the pressure decrease input 1244 will allow the device to pump fluid at a substantially constant pressure. For example, the infusion device may pump fluids maintaining the pressure between a range of about 0 mmHg and about 750 mmHg, and more preferably between about 25 mmHg and about 150 mmHg. For example, the user may select the pressure increase input 1242 until 45 mmHg is displayed in the selected pressure input 1246. During operation in this example, the dynamic range motor drive assembly will adjust the fluid flow rate to maintain, within a reasonable tolerance, for example, within 5%-20% of the selected pressure, a 45 mmHg pressure reading at the outflow pressure sensor.

A standard infusion input 1250, a rapid infusion input 1260, and a group of bolus preset inputs 1270 allow a user to select the infusion mode of the device. Selecting the standard infusion input 1250 will cause the device to pump fluid at a predetermined rate. For example, the device may, by default, pump 120 milliliters per hour when the standard infusion input 1250 is depressed. Similarly, selecting the rapid infusion input 1260 may cause the device to pump at a predetermined rate faster than the standard infusion, for example 500 milliliters per minute. The bolus preset inputs 1270 may include one or more buttons that, when selected, cause the infusion device to deliver a predetermined volume, for example, 100, 250, 500, or 1000 milliliters, of fluid at a predetermined rate, for example, at 500 milliliters per minute. The predetermined rate for each of the standard, rapid, and bolus infusion modes may be altered by the user by depressing the rate increase input 1280 or rate decrease input 1281. The rate increase and decrease inputs 1280, 1281 preferably only cause a small increment or decrement in the infusion rates, for example, between approximately 1 milliliter and 50 milliliters, preferably approximately 10 milliliters, each time the buttons are depressed. This allows a simple, but precise, control over the flow rates. Additionally, it may be preferable to also allow for a rapid rate increment or decrement when the rate increase and decrease inputs 1280,1281 are depressed and held. For example, if the rate increase input 1280 is held, the infusion rate may increase between approximately 10 and 500 milliliter increments or decrements, preferably approximately 50 milliliter increments, instead of 5 or 10 milliliters.

Depressing the start input 1285 will cause the pump device to begin operation in the selected mode. Similarly, the stop input 1286 will cause the pump device to stop delivering fluid. Additionally, it may be advantageous that the operation of the device, and the signals being sent from the above-discussed sensors, can be monitored so as to halt operation while unwanted behavior is encountered. For example, if the outflow bubble detector 112 senses air in the infusion tubing, a signal should be sent to the central controller to halt operation and signal to the user the nature of the problem encountered. Another example would be the outflow temperature sensor 140 detecting temperatures less than the desired temperature, thus causing the central controller to stop infusion and alert the user as to an error with the heat exchanger. Other examples of operating behavior that may cause an alarm and/or halt the device operation are, but not limited to: battery levels, excessive volume infused, motor failure, disposable not properly attached, pressure failures, computer/control unit failure, infusion line occlusion, and pump failure. It should be appreciated that the foregoing examples are for illustrative purposes, and that many other sensors and error handling routines may be implemented in the present invention, so as to at least cause a signal to be sent to the user and possibly to halt the operation of the device.

The user interface control panel 1200 may also cause indicators to be displayed showing the state in which the pump device is operating and certain selected parameters. For example, LED indicators may be mated with each of the above exemplary input options, so as to indicate which inputs have been selected. This gives the user a quick indication of the state in which pump device is operating. Additionally, there may be a selected rate indicator 1290, an actual rate indicator 1291, a selected pressure indicator 1246, and an actual pressure indicator 1248 that display to the user the flow rate and pressure selected by the user, and the actual flow rate and pressure of the device, respectively. These displays may be LED indicators, liquid crystal display indicators, or the like, as is known in the art. It is appreciated that other alerting mechanisms, such as beeps, alarms, tones, verbal warnings, or the like, as is known in the art, may be used by the present invention to indicate certain conditions and the severity thereof.

There may optionally be another status display panel 1205, in which the current operating data and any existing alarm indicators may be displayed, as also shown in FIG. 12. In this embodiment, the status display panel 1205 displays seven lines to the user in real-time. The panel may be constructed of a vacuum fluorescent display, liquid crystal display, or the like, as is known in the art. The status display panel 1205 may indicate, among others, the infusion mode selected, the heater status, the fluid temperature, the fluid pressure, the total amount of fluid infused, remaining volume and time for bolus infusion, and alarms or warning messages. It is appreciated that the aforementioned statuses are exemplary, and other statuses may be signaled to the user in the status display panel 1205.

Figure 13:
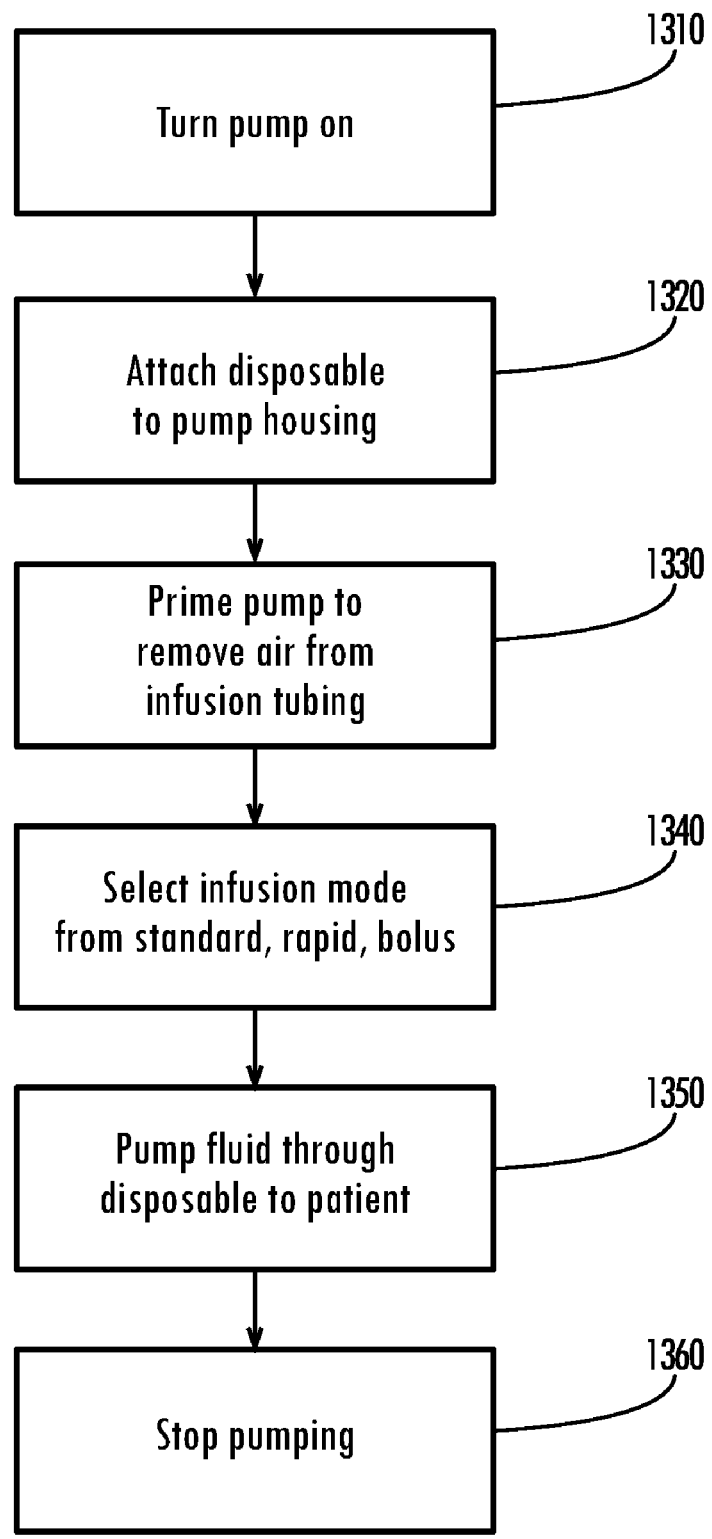
FIG. 13 shows an exemplary flow chart illustrating the steps of operation in accordance with an example of the present invention.
Figure 14:
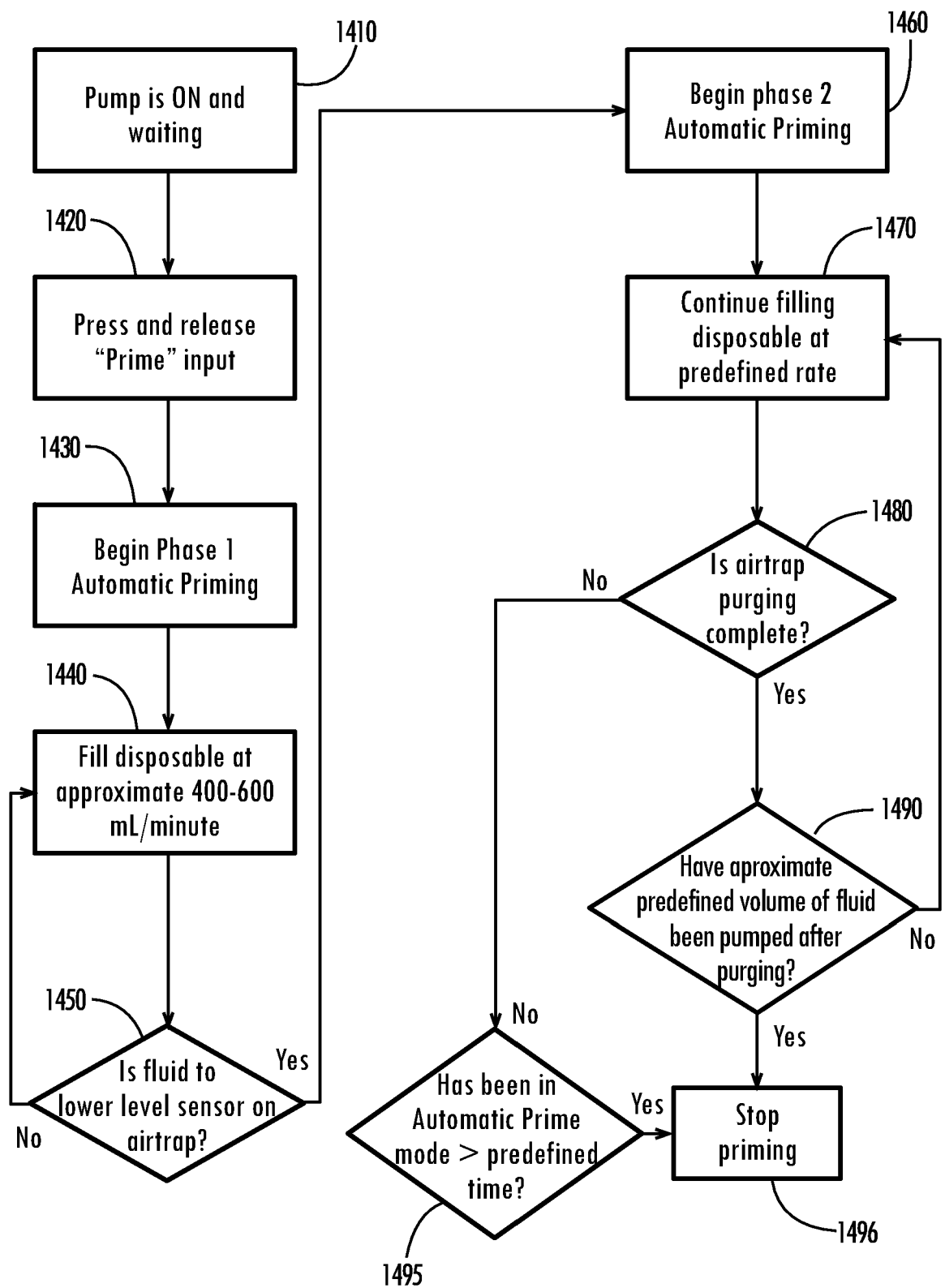
FIG. 14 shows an exemplary flow chart illustrating the steps to execute automatic priming in accordance with an example of the present invention.
Figure 15:
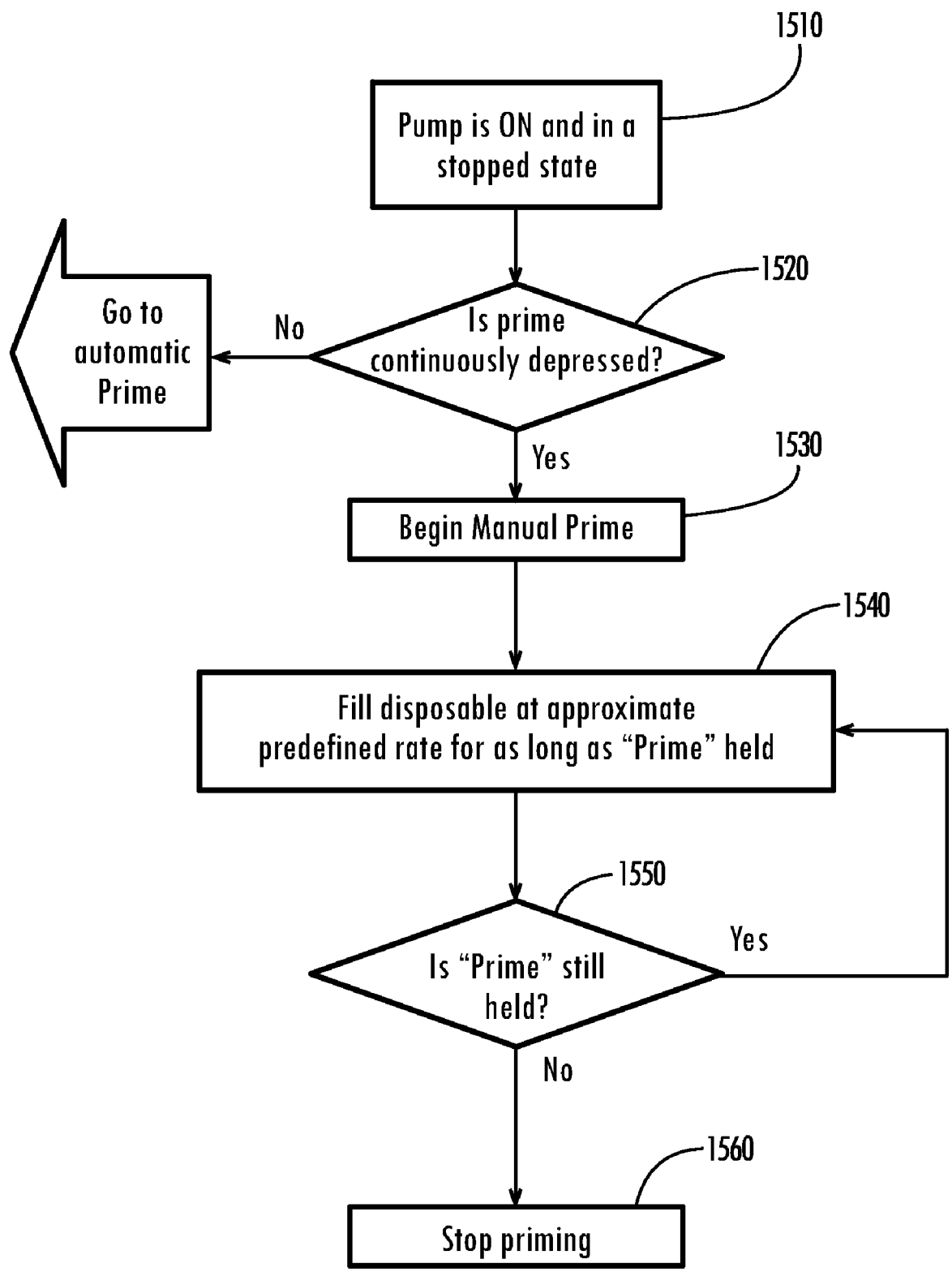
FIG. 15 shows an exemplary flow chart illustrating the steps to execute manual priming in accordance with an example of the present invention.

FIG. 13 provides a flowchart illustrating exemplary steps required for operation of the present invention. First, the pump may be turned on using the user interface control panel, as shown at block 1310. After turning on, the disposable cartridge is aligned with the pump housing and attached by engaging the engaging actuator, shown at block 1320. The pump device may be configured so certain functions are automatically activated upon attaching the disposable cartridge to the pump housing. For example, the device may default to a heating mode whereby the heating element is activated upon attaching the disposable. Block 1330 shows that before operation, the pump is preferably primed, so as to remove any air from the infusion tubing prior to delivery to the patient. The pump may be manually primed or may be automatically primed, as is illustrated in FIGS. 14-15. After priming, the pump may be operated in standard, rapid, or bolus infusion modes, as at blocks 1340-1350. Alternatively, the pump may be operated in a pre-selected pressure maintenance mode (not shown). As described above, the flow rates in each of these modes may preferably have a preset flow rate associated with it, but allow for changing the preset to a desired flow rate. Finally, the pump may stop pumping, as in block 1360, because of, among other reasons, the desired volume has been infused, an error on the device, or the stop input button is depressed.

Before entering into an infusion mode, the pump device is preferably primed. The pump device may be primed either automatically or manually. FIG. 14 shows exemplary steps that may be executed during automatic priming. After the device is on, in block 1410, depressing and releasing the prime input 1220 will cause the pump device to begin priming automatically, as is shown in blocks 1420-1430. Automatic priming may include two stages, a first stage, shown in blocks 1440-1450, during which fluid is pumped through the device until it reaches the lower level sensor of the air-trap, and a second stage, during which fluid is pumped at a greater rate, shown in blocks 1460-1470. The first stage may pump the fluid at a predefined rate, for example, between approximately 10 milliliters and 900 milliliters per minute, and preferably 500 milliliters per minute. The second stage may pump at a predefined rate, for example, between approximately 900 milliliters and 1200 milliliters per minute, and preferably 1000 milliliters per minute. The second stage may begin after fluid is detected by the lower level sensor, in block 1450, and continue until between approximately 10 milliliters and 100 milliliters, for example, about 35 milliliters, of fluid has been pumped after air purging through the air-trap is complete, as shown in blocks 1480-1490. If automatic priming is not complete in a predetermined period of time, for example ten minutes, an error shall be generated and the device shall stop priming, as is shown in blocks 1495-1496. Additionally, it is preferable that once a disposable has gone through automatic priming it does not go through automatic priming again.

FIG. 15 shows exemplary steps that may be executed during manual priming. After the pump is on, at block 1510, manual priming may be initiated by depressing and holding the prime input 1220, illustrated by blocks 1520-1530. While depressing the prime input 1220, the device may begin to fill the disposable at a predefined rate, for example, between about 10 milliliters per minute and about 1200 milliliters per minute, and preferably about 500 milliliters per minute, as is shown in block 1540. Block 1550 illustrates that the device will continue to prime manually until the user releases the prime input 1220. Upon release of the prime input 1220, the device will stop pumping, as shown in block 1560. After the device has been properly primed, it may begin infusion, as described above.

Figure 16:
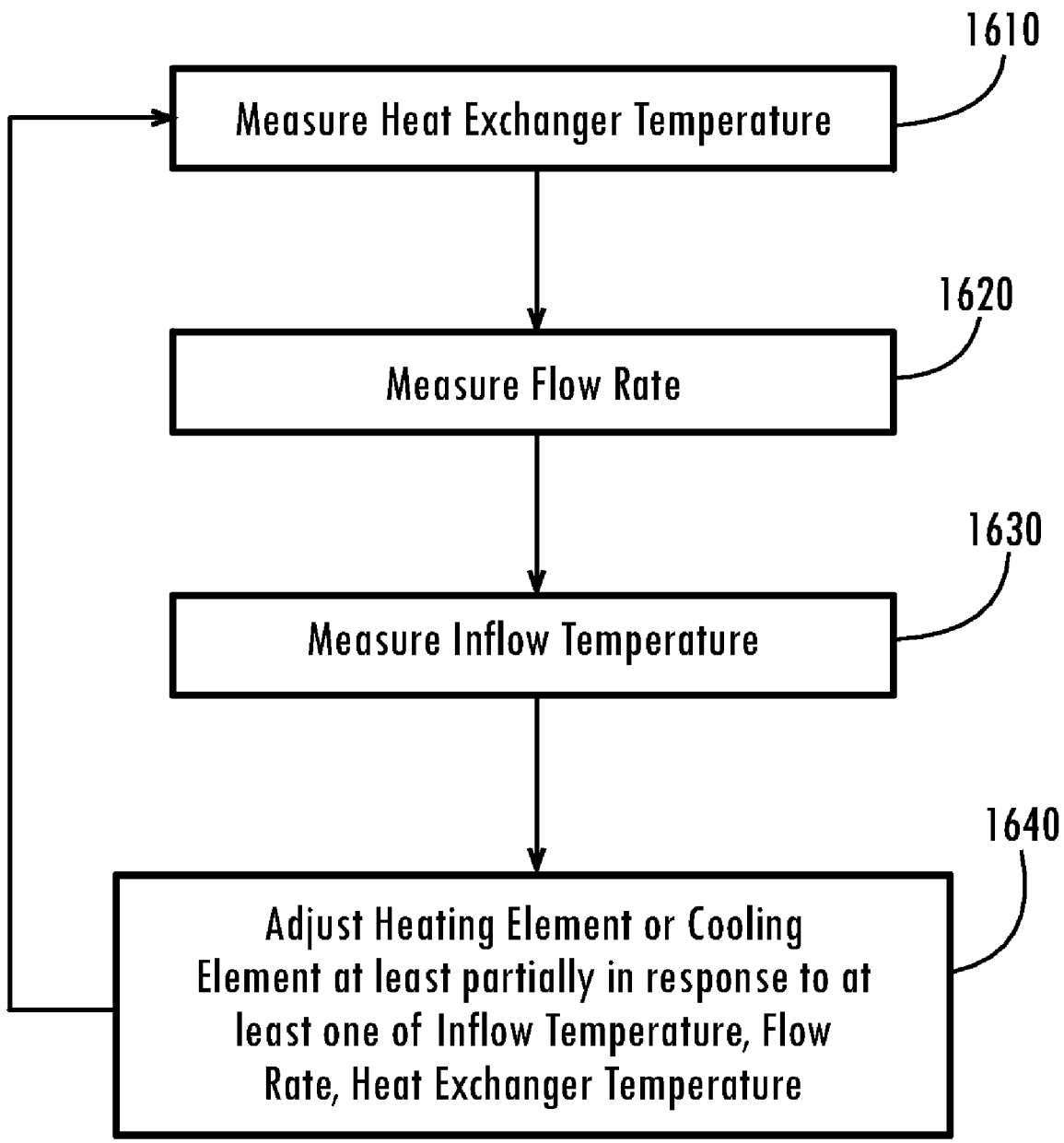
FIG. 16 shows an exemplary flow chart illustrating the steps to control temperature in accordance with an example of the present invention.

FIG. 16 shows exemplary steps that may be executed for controlling the thermal element, for example the heating element 810 or the cooling element 850, for warming or cooling the infusion fluid to the desired temperature. As noted above, heating or cooling a fluid within the heat exchanger is a function of the difference in mass between the fluid and the surrounding heat exchanger, the thermal conductivity of the fluid, the nature of the turbulence (mixing) of the fluid within the heat exchanger, the temperature differences between the heat exchanger and the fluid, and the duration of the fluid's presence within the heat exchanger.

The pump device operates to maintain the heat exchanger at a predetermined temperature, which may be sensed by the heat exchanger temperature sensor 287, as shown in block 1610, and further described in reference to FIG. 2d. Alternatively, the inflow temperature sensor 260 or the outflow temperature sensor 261 may sense the fluid temperature and be used, at least partially, to determine the thermal element operation. The central controller 1100 provides power to the heating element 810 or to the cooling element 850, as necessary, within the operating and safety limits of the device, to achieve a predetermined temperature. As a consequence of seeking the predetermined temperature, power is applied to the heating element 810 or cooling element 850, as is needed, raising or lowering the temperature of the heat exchanger 101, as shown in block 1640, and thus raising the temperature of a cool fluid passing through the heat exchanger 101, or lowering the temperature of a warm fluid. For example when warming fluid, at a given flow rate, say 200 ml/min, a colder fluid will take more energy out of the heat exchanger than a warm fluid when achieving an equilibrium temperature. Thus, the more heat transferred to the fluid, the less heat in the heat exchanger, resulting in a lower temperature reading at the heat exchanger temperature sensor, and requiring more power to be applied to the heating element to hold the predetermined temperature. The device operates similarly when cooling fluid by the heat exchanger using a cooling element—when the heat exchanger temperature sensor measures a greater temperature than the predetermined temperature, then power is applied to the cooling element to further cool the heat exchanger, drawing heat from the fluid therein.

In addition to maintaining the heat exchanger at the predetermined temperature, the central controller also takes into consideration the flow rate. At block 1620, the central controller receives the calculated flow rate of the infusion fluid from the dynamic range motor drive assembly, as further discussed in reference to FIGS. 10-11. Considering the flow rates allows compensating for any inherent lag in the system due to the mass of the heat exchanger and the speed of the reaction of the designed circuit.

At block 1630, the central controller receives from the inflow temperature sensor 260, as further discussed in reference to FIG. 2*d*, the temperature of the fluid prior to entering the heat exchanger. Considering the temperature of the fluid before heating or cooling allows compensating for the greater heat energy transfer required between the heat exchanger and the fluid during warming or cooling.

Thus, as occurs at block 1640, the central controller may consider at least one or a combination of the heat exchanger temperature, the inflow temperature, and the flow rate to cause proper adjustments in the heating element 810 or cooling element 850. For example, the greater the flow rates, the quicker the central controller adjusts to heat or cool to keep up with the flow rates. When the flow rates are slower, smaller adjustments are made by the central controller. Similarly, for greater temperature differences, the infusion fluid will have to be warmed, or cooled, at a higher, or lower, heat energy. The device configured in this embodiment may be used to heat infusion fluid to temperatures in the ranges from about 35° Celsius to about 50° Celsius, more specifically from about 37° Celsius to about 43° Celsius. The device configured in this embodiment may be used to cool infusion fluid to temperatures in the ranges from about 0° Celsius to about 37° Celsius, more specifically from about 4° Celsius to about 25° Celsius.

Example

Warming Fluid and Pumping at Variable Flow Rates

An embodiment of the infusion system under the present invention is shown in FIGS. 2*a-d*. The disposable cartridge 100 is shown with half of its outer cover removed in FIG. 2*a*. For orientation purposes, the air-trap 110 is visible, extending out of the outer cover 201 at the right-hand portion of the figure. The outer cover of the disposable is made of sturdy polymeric material. FIG. 2*b* shows the side of the disposable cartridge which will contact the pump housing 250, shown in FIG. 2*c*. Again, for orientation, the air-trap 110 is shown in FIG. 2*b* at the left-hand portion of the figure, extending out from the outer cover 201. The exposure surface 225 of the heat exchanger 101, which will be in contact with the heating platen 275 of the pump system heating element 810, is shown in FIG. 2*d*. FIG. 2*e* shows the pump housing, which contains a pumping mechanism 1020 to interact with the pump loop 104. FIG. 2*c* also shows the heating element 810, which provides the heat energy to the heat exchanger 101 contained within the disposable cartridge 100. All elements of this Example are in fluid connection with one another.

FIG. 2*d* illustrates how the disposable cartridge 100 may mate with the pump housing 250. The engaging actuator 280 allows the user to removably attach the disposable cartridge 100 to the pump housing 250 by the clamping mechanisms 290 that extend from lock housings 285 located about the platen 275. When the engaging actuator 280 is manipulated, the clamping mechanisms 290 contained within the lock housings 285 extend and engage the disposable 100 at attachment points 210 located about the exposure surface 225 of the heat exchanger 101. When engaged, the compressive force provided to couple the exposure surface 225 of the heat exchanger 101 to the heating platen 275 is from about 100 pounds to about 500 pounds, preferably about 200 pounds to 300 pounds, most preferably about 250 pounds, or alternatively about seven pounds per square inch, distributed substantially evenly across the exposure surface 225. Furthermore, because the pump may be used by operators under exceptional stress, and in which time is of the essence, a light-weight device, allowing for simple attachment of the disposable cartridge 100, provides substantial benefit. Located between the exposure surface 225 and the platen 275 is a thermal pad 840, which allows for extremely close and uniform contact between the platen 275 and the exposure surface 225, while still conducting heat at high efficiencies between the two surfaces. The material chosen as the thermal pad 840 may be a silicone-based pad, such as CHO-THERM T500®, supplied by Chomerics, located in Woburn, Mass. The thermal pad 840 allows for better heat transfer from the platen 275 to the heat exchanger 101 than an interface of air would allow. In this Example, the thermal pad 840 is about 0.01 inches thick and covers substantially the entire platen. Moreover, in this Example, the surface area of the exposure surface 225 contacting the heating the platen 275 is about 35 square inches. Attaching the thermal pad 840 to only the heating platen 275 is beneficial because the cartridge 100, being disposable, may be engaged and disengaged and replaced with a second cartridge 100, without disrupting the integrity of the thermal pad 840.

For the purposes of this Example, the fluid being infused into the patient is blood (although a similarly configured pump system may be used to deliver colloid, crystalloid, saline, medication, or the like). The fluid entering the pump system, embodied in this Example, may be around 20° Celsius. The rate at which infusion is conducted is about 1000 milliliters per minute. However, being driven by a motor, and controlled by an electronic controller, preferably a DSP controller, the rapid infusion system may be capable of pumping fluid at a rate of about 10 milliliters per hour to at least about 1200 milliliters per minute. Low speed operation could be used for routine IV (intra-venous) infusion; and high speed operation would be used for rapid fluid infusion for cases such as emergency room trauma. Additionally the device can be particularly advantageous in situations where it may be preferable to first employ routine IV infusion, followed by rapid infusion, followed again by routine infusion, such as during a transplant operation. It is also appreciated that in some embodiments, for example during emergency heart and lung support procedures, it may be preferable to infuse blood at rates as great as about, 2000 milliliters per minute to about 8000 milliliters per minute.

Conventional IV fluid, or blood bags or bottles, can be used, for example, or an alternate fluid reservoir can be employed, particularly when large quantities are to be infused. The bags or bottles are spiked with a delivery tubing that is connected to the disposable cartridge. The disposable cartridge is aligned and attached to the front of the pump housing, with pumping mechanism extending through the attached disposable cartridge, and communicating with the pump loop.

After the disposable cartridge 100 is attached to the pump housing 250, aligning and engaging each of the cartridge components and sensors with their mates, the roller pumphead of the pumping mechanism may apply pumping pressure to the pump loop 104, causing fluid to flow from a fluid source through the cartridge, and infusing at the desired rate.

The user may turn the pump device on by depressing the power input 1210. Next, after turning on, and before infusing fluid, the device shall be primed. The user may use automatic priming by selecting the prime input 1220, or the user may prefer to hold down the prime input 1220 so as to cause the device to be manually primed for as long as the user holds down the device. Priming is successful after air has been purged from the fluid path, and substantially all the way to the end of the patient outflow line, by automatic or manual priming. The user may then choose to either infuse at a standard adjustable rate by selecting the standard infusion input 1250, infuse a bolus of either 100 milliliters, 250 milliliters, 500 milliliters, or 1000 milliliters at an adjustable rate initially set to 500 milliliters per minute, by selecting one of the bolus preset inputs 1270, or infuse at a rapid adjustable rapid rate by selecting the rapid infusion input 1260. In one embodiment, the heat is on in the default setting; thus the user does not have to select anything to begin heating the fluid. Accordingly, the user may turn off the heating mode by deselecting the heat input 1230. Alternatively, in another embodiment, the heat may not be set to on in the default setting and the user thus may turn the heating mode on by selecting the heat input 1230, and similarly turn it off by selecting it again (or deselecting it). After the device is primed and the desired infusion mode and infusion rates are set, infusion begins when the user selects the start input 1285. The user may vary the infusion rate by selecting the rate increase input 1280 or rate decrease input 1281, which causes the electronic controller to advantageously increase or decrease the pump rate accurately to the selected, or default, infusion rate. Upon receipt of the signal from the user interface, for example, for rapid infusion with an increased rate of 1000 milliliters per minute, the electronic controller 1110 sets its PWM signal duty cycle for transmission to the motor power drive circuitry 1120, to turn the motor drive assembly at the appropriate speed. For example, to achieve a T000 milliliter per minute flow rate with a pumping mechanism 1020 that provides 3 milliliters of fluid per revolution and a motor that is connected to a 14:1 gear assembly 1030, the motor needs to turn at 4667 revolutions per minute.

While pumping under this scenario, LED indicators would be powered next to the rapid infusion input, the chosen maximum pressure input, and the heat input on the user interface panel 1200. Additionally, the selected rate indicator 1290 would display 1000, and the actual rate indicator 1291 would display the rate the infusion device is actually pumping. Similarly, the status display panel 1205 may indicate that the device is operating in rapid infusion mode, the heat is on, the sensed temperature of the blood, the sensed pressure of the blood in the infusion tubing, as well as the total volume infused.

Again, referring to FIG. 1, the blood is drawn into the primary in-flow tube 102 and proceeds past the inflow bubble detector 120, which sends a signal to the central controller of the device if excessive bubbles or air is sensed in the infusion fluid. After passing the inflow bubble detector, the blood passes the inflow temperature sensor 260, allowing for proper feedback and temperature regulation. Next, the blood will pass a t-junction, which serves as the inflow pressure junction 103. The inflow pressure junction 103 is in fluid communication with a first air chamber 151. The inflow pressure junction 103, in combination with the first air chamber 151 and the inflow pressure sensor 270, determines the pressure of the blood flow as it enters the pump loop 104, to allow for proper regulation of the blood flow.

The inflow pressure junction 103 monitors negative pressure, in the event that fluid remains within the disposable cartridge but is not flowing in the direction of the patient. Such a circumstance could arise if the fluid source bag collapses, yet fluid remains in the cartridge. If the pressure at the inflow pressure junction 103 falls below a predetermined pressure, for example, approximately 1 mmHg, then the pump may stop pumping.

When the blood leaves the pump loop 104, it flows through a second t-junction, which serves as the pump outflow pressure junction 105. The pump outflow pressure junction 105, in combination with another air chamber and the pump outflow pressure sensor 271, determines the pressure of the blood as it exits the pump loop 104, so that the flow of the blood through the disposable cartridge 100 can be regulated. The pump outflow pressure junction measures the pressure of the fluid proceeding through the cartridge. Here, blockage is monitored, so that when the pressure exceeds a predetermined pressure, for example, approximately 500 mmHg, the pump may shut down to avoid damage.

The blood then passes into the heat exchanger 101 via the exchanger inlet port 106. The heat exchanger 101 of this Example is created from two halves, as depicted in FIG. 3. The two halves are created from the same mold, such that inverting one mold and fixing the two together creates the heat exchanger. Both halves are created from the same highly conductive material to maximize the conductive surface area against which the blood will flow, thus maximizing the transfer of heat from the heat exchanger 101 to the fluid. The material used in the creation of the heat exchanger of this Example is anodized aluminum. The use of this material accomplishes the goal of the present invention by creating a large mass differential between the heat exchanger and the fluid, blood, to be warmed. The thermal conductivity of the anodized aluminum allows for excellent dissipation of heat energy across the heat exchanger. The anodized surface of the aluminum creates a biologically inert surface to prevent either the reaction with, or adsorption of, biological material, while the blood or other fluid passes across it. In the present Example, dealing with blood, protein adsorption to the surface of the material may generate a trigger to the clotting cascade. The adsorbed proteins to the inner surface of the heat exchanger, even if they do not trigger the clotting cascade, can become degraded and detach. Once detached from the surface of the heat exchanger, these degraded, or denatured, proteins may react with other proteins, or the cells contained within the blood, in a deleterious manner. The anodized inner surface of the heat exchanger thus prevents damage from occurring to the blood as it passes through the heat exchanger.

When a disposable cartridge according to the present invention is used, the effective exchange of heat, from the heat exchanger to the fluid being infused, achieves the appropriate rise in temperature of the fluid, without having to expose the fluid to potentially dangerous temperatures, as defined as a predetermined temperature limit. Instead of having regions of varied temperature, to which the blood or fluid is exposed, the heat exchanger's constant temperature allows for more efficient transfer of heat energy to the blood. At a flow rate of 1000 milliliters per minute, achieving a fluid exit temperature of 37° Celsius means never having to expose the blood to temperatures which could be deleterious to the fluid being infused. In fact, using anodized aluminum yielded a 95-96% efficiency in transferring heat energy to blood, sufficient to generate a 17° Celsius rise in temperature.

Once the blood enters the heat exchanger, the blood fills the flow cavity 304 before proceeding to traverse the entirety of the heat exchanger. The blood fills the flow cavity first, because of the narrower flow area created by the flow fin 303 which defines the flow cavity. By creating a smaller flow path to flow over the first fin, as depicted in FIG. 7, the blood will not traverse the long axis of the heat exchanger before it fills the flow cavity, causing the flow pattern across the heat exchanger's fins to be a wide ribbon-like shape.

The fins used in the heat exchanger, described in FIGS. 2a-d, are spaced at about 0.4 inches apart. The depth of the flow path created by the separation of the two pluralities of fins is about 0.08 inches. The fins are about 4.3 inches wide and 0.62 inches in height. This creates a ratio of linear flow distance to width of about 1:7. The flow fin 303, as seen in FIG. 3, is wider than the remainder of fins across the heat exchanger. That increased width of the flow fin 303 creates a narrower flow path at that fin when the two halves of the heat exchanger are connected. In this Example, the width of the flow path created by the flow fin 303 is about 0.03 inches. Given that the blood flowing through the heat exchanger in this Example will preferably travel along a path of least resistance, the flow cavity 304 will fill before the blood travels past the flow fin 303. The blood then travels over the fins which creates a turbulent flow pattern for the blood as it travels through the heat exchanger. This turbulent flow ensures an increased exposure of more molecules within the blood fluid to the heat exchanger, thereby increasing the efficient transfer of heat energy.

Once the blood flow reaches the top of the heat exchanger, it exits via the exchanger outlet port 107 located a position opposite the exchanger inlet port 106 of the heat exchanger 101. At this point, the fluid for infusion has undergone warming and the desired temperature has been reached. The heat exchanger temperature sensor 287 measures the temperature of the heat exchanger 101 and provides feedback to the central controller for effective temperature regulation. The blood then enters the air-trap 110 at a location approximately midway between the top and bottom of the long-axis of the air-trap 110. In this Example, the air-trap is about 4.2 inches along its long, vertical axis and about 1 inch in diameter. The air-trap intake port 503 is located about 2.1 inches from the bottom of the air-trap (see FIG. 6). As the blood passes through the air-trap intake port, the blood travels in a clockwise direction as the blood fills the air-trap. This clockwise flow of blood creates a vortex of fluid in the air-trap. The fluid flow disrupter 601, which, in this example, extends from the interior surface of the bottom of the air-trap up about 0.5 inches, creates a sufficient pressure differential at the fluid output port 505 to draw the blood out and not any trapped air.

Air may become trapped in the blood in this Example via several mechanisms. Through spiking the blood, as it is attached to the pump system for infusion, trapping air and in essence failing to properly purge the source of the blood before attachment to the system. Also, the heating of the fluid itself can cause the release of stored gas within the blood, which may be deleterious if introduced into the patient.

As the amount of air in the air-trap 110 increases, the level of blood in this Example, lowers within the air-trap. When the blood is below the upper level sensor interface 507 and the lower level sensor interface 506, which, in this Example, are ultrasonic sensors that communicate with the upper level sensor 246 and the lower level sensor 245, respectively, in the pump housing the level of fluid in the air-trap, the valve at the fluid output port 505 closes. When the fluid outflow flow limiting mechanism 240 is closed, compressing the primary outflow tube 108, the air output flow limiting mechanism 241 is open. This increases the blood volume in the air-trap, forcing air out of the air output port 504. The lower level and upper level ultrasonic sensors 245, 246 are located in the pump housing 250. The ultrasonic sensors utilize energy transmitting material, for example, silicone or urethane pads, to facilitate the transmission of the sensor signals to the lower level sensor interface 506 and the upper level sensor interface 507, in order to effectively couple and measure the level of fluid within the air-trap. When the level of blood rises to or above the upper level sensor interface 507, and thus also above the lower level sensor interface 506, the air output flow limiting mechanism 241 closes. At approximately the same time that the air output flow limiting mechanism 241 closes, the fluid outflow flow limiting mechanism 240 opens, and blood exits the air-trap and proceeds toward the patient.

In this Example, the fluid then passes through the fluid outflow pressure junction 135, which assists in determining the pressure for controlling the flow within the cartridge when based on pressure. If there is blockage, and the pressure begins to rise, this device will try to keep the pressure within an acceptable range, which can be between approximately 0 mmHg and the predetermined upper limit, which in this Example may be either 100 mmHg or 300 mmHg, depending upon what is selected by the user, by adjusting the flow rates. For example, during operation, the central controller will cause the dynamic range motor drive assembly to pump fluid to achieve the pre-selected rate by the user. However, if the pressure limit is reached, the dynamic range motor drive assembly will slow, allowing the pressure to fall and then speed up again to reach the rate. If the pressure at the fluid outflow pressure junction 135 rises above a predetermined safety level, possibly different than that level selectable by the user, for example, 500 mmHg, the pump may shut down.

In the present Example, however, before blood reaches the patient, it passes through the outflow bubble detector 112. The outflow bubble detector analyzes the blood on its way to the patient to determine that the air-trap removed potentially deleterious air from the system. The bubble detector in this Example uses an ultrasonic sensor, which sends a signal across the tube. Any air bubbles present in the system will attenuate the signal. The system will shut the pump down if bubbles as small as 30 to 50 microliters are detected. The system is able to detect bubbles of this size at the maximum flow rate of, for example, 1200 milliliters per minute (in the intravenous fluid infusion example).

After passing through the outflow bubble detector 112, the fluid outflow temperature sensor 261 uses infrared temperature detection to measure the temperature of the blood before being delivered to the patient. This allows for a final temperature verification of the fluid (e.g., the blood), so as to avoid delivering overheated fluid to the patient.

Finally, after infusion, the disposable cartridge 100 may be removed from the pump housing 250 and may be discarded. A new disposable cartridge 100 may then be attached to the same pump housing 250 for subsequent use. The disposability of the heat exchanger is beneficial in settings in which quick turn-around is necessary between uses, by avoiding sterilization after each use. Also, the disposable cartridge of the present invention, being a self-contained heating device, promotes a sterile surgical field, by removing external heating mechanisms and avoiding the introduction of unnecessary foreign fluids.

Unlike standard or traditional methods of intravenous fluid administration, the rapid infusion system described herein can provide continuous total replacement of adult human blood volume through virtually any sort of hemorrhage, for an indefinite period of time, and can rapidly regulate fluid temperature with minimal increase in resistance to flow. Additionally, the device can easily and rapidly administer massive quantities of blood to a single patient during a single operation, administer physiologic fluid maintained at a predetermined temperature, at flow rates as great as 1200 milliliters per minute (or greater in other examples), and permit simultaneous display and control of fluid temperature. The system can easily be carried, and is able to be quickly and easily used in emergency situations or by emergency personnel in the field. The system can be configured to infuse an infinite amount of blood over an indefinite period of time, based on the pump assembly employed, the tubing sizes, etc., employed.

Further, the system described in this Example may be used to infuse blood at a temperature greater than the patient's body temperature, as is advantageous in certain therapies, such as during the treatments of viruses, for example, the hepatitis C virus. In an embodiment used to warm blood for therapeutic effects, such as systemic warming during the treatment of the hepatitis C virus, the blood may be warmed to temperatures between about 37° Celsius and about 48° Celsius prior to infusion to the patient. This procedure may be repeated one or more times, allowing the patient to cool in between each successive infusion of warmed blood. The infusion target for warming the patient may be generally directed for systemic warming of the patient's core, or, alternatively, warming may be targeted to a specific region or organ, such as, for example, the liver.

If desired, the present invention can include multiple pumps infusing fluid to a patient through multiple catheters, thereby providing such fluids to the patient in volumes which far exceed that possible by present infusion systems.

Example

Cooling Fluid

In another embodiment, the pump device may be used to cool, rather than warm, blood or other fluid being delivered to a patient. This may be particularly useful for patients suffering from an acute stroke, for example, to controllably induce hypothermia by cooling the infused blood. This embodiment operates much like the embodiment described in the previous example, except that it includes a cooling element 850, as shown in FIG. 5*b*, instead of a heating element.

In this embodiment, the cooling element 850 cools the heat exchanger 101, including the plurality of fins housed therein, to a temperature lower than its ambient temperature before infusion. The infusion device of this embodiment may cool infusion fluid to temperatures between about 0° Celsius and about 37° Celsius, more preferably between about 4° Celsius and about 25° Celsius. In this example, blood is cooled to, and maintained at, a temperature of about 20° Celsius while flowing through the heat exchanger 101. After continuing through the same flow path through the entire disposable cartridge, the cooled blood is then infused to the patient, for example, to the brain region. Note, however, that cooled blood, or other infusion fluids, may be infused to other regions of a patient, which will similarly induce a controlled hypothermia. In another example, cooled blood may be intravenously infused to a region near the heart for a patient suffering from an acute myocardial infarction.

In one variation of this embodiment, the pump device may contain a heating element 810 and a cooling element 850 both, as described by this example. The disposable cartridge may be attached to the pump housing, so as to align with the heating element 810, or the disposable cartridge may be attached to the pump housing, so as to align with the cooling element 850. Thus, in this configuration, the pump device may be controlled so as to allow the user to either deliver warm or cool blood during operation. This configuration would be advantageous for procedures that benefit from interchangeably delivering volumes of warmed blood and cooled blood, or for warming blood to a desired temperature, for example, 43° Celsius, and then cooling back to body temperature (i.e., 37° Celsius), or vice versa. It is further appreciated that a second disposable cartridge, or a single disposable cartridge with a second heat exchanger, may be included with the pump system, with one heat exchanger delivering warmed fluid and another delivering cooled fluid.

In yet another variation, the pump device may have an interchangeable heating element and cooling element. In this configuration, the cooling element, including the thermoelectric coolers, heating platen, and thermal pad, can replace, at will, the heating element, including the power insulators, power resistors, heating platen, and thermal pad. It is appreciated that only the assembly housing the power insulators and power resistors, and the assembly housing the thermoelectric coolers may be removable, leaving the heating platen and thermal pad remaining in the pump housing. This interchangeable configuration is advantageous because it allows for rapid switching between providing cooling and warming capabilities while still maintaining the small size that beneficially allows simple operation.

Example

Body Temperature Regulation

In yet another embodiment, the pump device may be used to deliver large quantities of fluid in a controlled manner, and at a controlled temperature, through the body to assist in controlling the patient's core body temperature. Certain procedures benefit from, or are positively affected by, controllably inducing hypothermia.

In one example, saline solution is pumped through the heat exchanger including a cooling element 850, as in the previous example, for ultimate delivery to a patient suffering from an acute myocardial infarction. The saline solution may initially be stored at room temperature, for example, about 20° Celsius to about 22° Celsius, and is preferably cooled between about 0° Celsius and about 15° Celsius. In this example, saline is cooled, for example, to about 10° Celsius prior to infusion. The cooled saline solution is then delivered to the patient's bladder using a catheter. A double lumen or triple lumen catheter may be used for delivering cooled saline therethrough, and into the bladder and replacing previously delivered fluid by evacuation through the catheter. In this example, the patient's bladder is cooled because it has a relatively large volume and is centrally located, providing a quicker, and more controlled means to cool one's core temperature.

In another variation, the saline solution may be warmed, instead of cooled, using a heating element in the pump housing, as in the first example above. Delivering warmed fluid into a centrally located volume may be helpful, for example, when a patient is recovering from a surgical procedure under anesthesia, or when a patient is suffering from extreme hypothermia.

Alternatively, rather than utilizing the cooling or warming capabilities of the pump device, pre-cooled or pre-warmed fluid may be delivered to cool or warm a patient's core temperature. In this embodiment, the pump device is beneficial for controlling the flow rates and pressures, including the ability to deliver pre-warmed or pre-cooled fluids at a wide range of flow rates. Controlling the flow rates will further allow more precise control of the patient's core temperature.

It is appreciated that, in this embodiment, sensing and preventing air in the fluid path is unnecessary. The bubble detectors and air-trap may be disabled while the device is used in this embodiment.

Example

Pressure Maintenance

In yet another embodiment, the pump device may be operated as in any of the previous examples, however, the pump device may maintain a substantially consistent flow pressure. The pump device in this embodiment may maintain a relatively constant pressure, between a range of about 0 mmHg and about 750 mmHg, and more preferably between about 25 mmHg and about 150 mmHg. This embodiment is particularly advantageous during certain surgical procedures, such as endoscopic procedures, like arthroscopic or laparoscopic surgeries. During an arthroscopic surgery, for example it is desirable to deliver fluid to expand the joint, as well as to flush the surgical area and to tamponade bleeding vessels. It may also be desirable to warm the fluid to avoid unnecessary cooling of the surgical region.

Saline solution may be used as the fluid delivered in this embodiment. Each of the steps described in the first example to prepare the pump device for operation, such as attaching the disposable cartridge and selecting the desired inputs, are carried out. However, under this embodiment, the user preferably selects either the pressure increase input 1242, or the pressure decrease input 1244, on the user interface panel 1200 to pre-select the desired flow pressure maintenance level. Upon selecting one of the pressure inputs, the selected pressure indicator 1246 displays the pressure selected. In this example, the user selects the pressure increase input 1242 until 45 mmHg is displayed on the selected pressure indicator 1246. Additionally, the user may select the heat input 1230 to cause the saline solution to be warmed while circulating through the heat exchanger 101 prior to delivery to the patient. Finally, the primary outflow tube 111 is connected, via surgical tubing, such as silicon tubing, to an inflow cannula, or the like, as is typically used during arthroscopic or laparoscopic procedures. The cannula is inserted into the patient at or near the joint to allow accurately controlling the delivery of the fluid.

Upon beginning operation, the pump device generally operates as described in the first example, warming the saline solution prior to delivery via the cannula to the patient. However, the pressure may be substantially maintained at a selected pressure—here 45 mmHg—by the device central controller 1100, causing the electronic controller 1110 to adjust the motor speed, thus adjusting the flow rate to substantially maintain a flow pressure of 45 mmHg at the pre-selected desired flow rate. A feedback loop exists from the fluid outflow pressure junction 135 to the dynamic motor drive assembly, via the device central controller 1100, which will allow continuous adjustments to be made to the dynamic motor drive assembly to maintain the constant pressure. It is further appreciated that during operation, the pressure maintenance levels may be changed by selecting one of the pressure increase input 1242 or the pressure decrease input 1244. The device used in this embodiment may preferably deliver flow rates between about 0 milliliters per minute to about 2000 milliliters per minute.

Example

Cardiopulmonary Bypass or Assist

In yet another embodiment, the pump device described herein may be used with patients undergoing cardiotomy, and requiring at least partial cardiopulmonary bypass or suffering from organ (heart and/or lung) failure or deterioration. The device used in this embodiment may maintain blood circulation while preferably oxygenating the blood prior to infusion (or re-infusion). Examples of uses for which a device configured for this embodiment may be used are to provide cardiac bypass during cardiac surgery, cardiac assist, extra-corporeal membrane oxygenation, during percutaneous heart valve replacement procedures, or during the treatment of pneumonia, sepsis (treating and/or supporting resulting organ failure), acute respiratory distress syndrome, emphysema, chronic bronchitis, asthma with status asthmaticus, neonatal respiratory distress syndrome, smoke inhalation, or burn victims (treating and/or supporting resulting organ failure).

A device configured for use in this embodiment may include a pumping mechanism, a dynamic range motor drive assembly, and a central controller, as described herein. Further, the device preferably includes an oxygenator in line with the infusion path. The fluid flow circuit may preferably be configured as a closed circuit, whereby blood is drawn from the patient, pumped through the pump device, pumped through the oxygenator, and then re-infused to the patient. The oxygenator may be placed distal to the dynamic range motor drive assembly prior to infusion to the patient. The oxygenator may be a bubble oxygenator, a membrane oxygenator having multiple capillary tubes creating membranes between the blood and the gas, or the like, as is known in the art. The pumping mechanism may be a roller head occlusive pump, a non-circular peristaltic pump, a centrifugal or conical pump, an impeller, or the like, as is known in the art. The dynamic range motor drive assembly, the pumping mechanism, and the electronic controller are preferably configured, so as to provide infusion flow rates up to at least 8000 milliliters per minute, preferably between about 2000 milliliters per minute and about 4000 milliliters per minute. It is appreciated that a pump device, configured for cardiopulmonary bypass or assist, may also be able to deliver fluids to a patient at slower flow rates, like those described above, such as flow rates as low as 1 milliliter per hour. The infusion flow pressure may also be monitored and controlled as described above. The pump device may also include an air-trap, so as to capture bubbles in the blood before infusion, and a thermal element, such as a heating element and/or a cooling element, as described above, so as to allow cooling or heating the blood prior to oxygenation and delivery to the patient. A pump device used in this embodiment is particularly advantageous because of its manageable size and simple operation, while allowing a wide range of infusion flow rates.

Example

Dialysis

In yet another embodiment, the pump device, described herein, may be used during renal replacement therapy, such as kidney dialysis, to treat patients with renal impairment or failure. Accordingly, this embodiment may be used to circulate cleansed or filtered blood through a patient.

A device configured for use in this embodiment may include at least two pumping mechanisms, at least two dynamic range motor drive assemblies, a central controller, and a dialysate bath. Accordingly the blood may be pumped by one pumping mechanism and motor drive assembly through multiple capillary tubes, forming a semi-permeable membrane between the dialysate bath and the blood, as is known in the art. The dialysate may be pumped by another pumping mechanism and motor drive assembly across the capillary tubes in a direction opposite of the direction the blood is pumped through the capillary tubes, so as to create a counter current bath of osmotic fluid. The osmotic fluid or dialysate may include the same, or higher, levels of physiologic electrolytes, such as salts, as normally exist in blood, so as to force undesired solutes from the blood to the dialysate through osmosis. Further, the dialysate may include higher levels of bicarbonate than normally exist in the blood, so as to force bicarbonates from the dialysate to the blood, thereby reducing acidosis, if so desired. The blood flow circuit may preferably be configured as a closed circuit, whereby blood is drawn from the patient, pumped through the pump device, pumped through the dialysate bath, and then re-infused to the patient. The dialysate bath may be configured as a closed circuit or an open circuit, allowing for reuse of the dialysate, or for replenishing used dialysate with fresh dialysate, so as to maintain consistent electrolyte concentrations. A device configured for use in this embodiment may provide simple infusion flow rate control over the entire range, as disclosed herein, as well as simple dialysate bath flow rate control. The infusion flow rate may preferably range from about 200 milliliters per minute to about 700 milliliters per minute, more preferably from about 300 milliliters per minute to about 500 milliliters per minute. Though, it is appreciated that a pump device configured for dialysis procedures may also be able to deliver fluids to a patient at slower flow rates, such as 1 milliliter per hour, or faster flow rates, such as up to 8000 milliliters per minute, as further described herein. Similarly, the flow pressure of both the dialysate and the blood infusion may also be controlled as described herein. Like described above, the device may also include an air-trap and a thermal element. Such as a heating and/or cooling element. A pump device configured for use during dialysis procedures is particularly advantageous because of its portability, relative low cost, ease of use, and its robust features such as variable flow rates, heating and/or cooling, and utilizing an active air-trap.

The above description is intended to be illustrative and not restrictive. Many embodiments will be apparent to those of skill in the art upon reading the above description. The scope of the invention should therefore be determined not with reference to the above description, but should instead be determined with reference to the appended Claims, along with the full scope of equivalents to which such Claims are entitled. The disclosures of all articles and references referred to herein, including patents, patent applications, and publications, are incorporated herein by reference.

What is claimed is:

1. A pump system, comprising:
   a. a pump housing comprising a motor driven pump, a user-selectable prime input, a user-selectable infusion input, and a central controller in communication with said prime input, said infusion input, and said motor driven pump; and
   b. a cartridge removably coupled to said pump housing comprising at least one infusion tubing and an air-trap in fluid communication with said at least one infusion tubing;
   wherein:
      said central controller is configured to automatically prime said at least one infusion tubing by causing said motor driven pump to pump fluid through said at least one infusion tubing at a first positive flow rate and at a second positive flow rate different than the first flow rate when fluid reaches a predetermined level in said air-trap in response to the selection of said prime input; and
      said central controller is further configured to cause said motor driven pump to pump fluid through said at least one infusion tubing and said air-trap to a patient in response to the selection of said infusion input.

2. The pump system of claim 1, wherein:
   said at least one infusion tubing comprises a first infusion tubing, a second infusion tubing, and an air output tubing;
   said first infusion tubing carries fluid in to said air-trap, said second tubing caries fluid out of said air-trap, and said air output tubing allows air to exit said air-trap;
   said pump housing further comprises a fluid outflow flow limiting mechanism that reversibly restricts the flow of fluid through said second infusion tubing and an air output flow limiting mechanism that reversibly restricts the flow of air through said air output tubing; and
   said central controller causes said fluid outflow flow limiting mechanism to restrict the flow of fluid through said second infusion tubing and causes said air output flow limiting mechanism to allow the flow of air through said air output tubing in response to the selection of said prime input.

3. The pump system of claim 2, wherein said fluid outflow flow limiting mechanism and said air output flow limiting mechanism comprise pinch clamps that operably and reversibly engage and compress said second infusion tubing and said air output tubing, respectively, when actuated so as to prevent the flow of fluid or air at the points of compression.

4. The pump system of claim 1, wherein said central controller is further configured to manually prime said at least one infusion tubing by causing said motor driven pump to begin pumping fluid at a third flow rate into said air-trap to remove air from said at least one infusion tubing while said prime input is depressed and to stop said pumping fluid when said prime input is released.

5. The pump system of claim 4, wherein said third flow rate is between about 100 milliliters per minute to about 1200 milliliters per minute.

6. The pump system of claim 4, wherein said third flow rate is approximately the same as the first flow rate or the second flow rate.

7. The pump system of claim 4, wherein said third flow rate differs from the first flow rate and the second flow rate.

8. The pump system of claim 1, further comprising a lower level sensor and an upper level sensor aligned with said air-trap and in communication with said central controller, wherein:
   said lower level sensor detects fluid at a first point in said air-trap;
   said upper level sensor detects fluid at a second point in said air-trap;
   said first point is positioned distal to said second point in said air-trap; and one of the first point or the second point indicates the predetermined level in said air-trap that, when reached by the fluid, the motor driven pump adjusts the flow rate through said at least one infusion tubing.

9. The pump system of claim 1, wherein said central controller automatically primes said at least one infusion tubing in response to depressing and releasing said prime input.

10. The pump system in claim 1, wherein said first flow rate is between about 10 milliliters per minute to about 900 milliliters per minute.

11. The pump system in claim 1, wherein said second flow rate is between about 900 milliliters per minute to about 1200 milliliters per minute.

12. The pump system of claim 1, wherein the second flow rate is greater than the first flow rate.

13. The pump system of claim 1, wherein at least one of the first flow rate or the second flow rate is between about 10 milliliters per minute and about 1200 milliliters per minute.

14. The pump system of claim 1, wherein said central controller causes said motor driven pump to stop pumping after fluid reaches the predetermined level in said air-trap.

15. The pump system of claim 1, wherein said central controller causes said motor driven pump to stop pumping after pumping for a predetermined period of time.

16. The pump system of claim 1, wherein said central controller causes said motor driven pump to stop pumping after pumping a predetermined volume of fluid.

17. The pump system of claim 1, wherein the predetermined level is a first predetermined level, and wherein said central controller causes said motor driven pump to stop pumping after reaching a second predetermined level proximal the first predetermined level.

18. The pump system of claim 1, wherein the predetermined level is a first predetermined level, and wherein, upon reaching a second predetermined level proximal the first predetermined level, said central controller causes said motor driven pump to stop pumping either (a) after pumping for a predetermined period of time or (b) after pumping a predetermined volume of fluid.

* * * * *